United States Patent [19]
Strohl et al.

[11] Patent Number: 5,962,293
[45] Date of Patent: Oct. 5, 1999

[54] METHODS OF PRODUCING DOXORUBICIN

[75] Inventors: William R. Strohl, Dublin; Michael L. Dickens; Charles L. Desanti, both of Columbus, all of Ohio

[73] Assignee: The Ohio State Research Foundation, Columbus, Ohio

[21] Appl. No.: 09/096,982

[22] Filed: Jun. 12, 1998

Related U.S. Application Data

[62] Division of application No. 08/653,650, May 14, 1996.

[51] Int. Cl.$^6$ ....................................................... C12N 9/02
[52] U.S. Cl. ...................... 435/189; 435/183; 435/252.3; 435/252.33; 435/320.1; 536/23.2
[58] Field of Search ................................. 435/189, 252.3, 435/252.33, 252.35, 320.1; 536/23.1, 23.2, 23.7, 23.74

[56] References Cited

U.S. PATENT DOCUMENTS

| | | | |
|---|---|---|---|
| 5,008,380 | 4/1991 | Palladino et al. | 536/6.4 |
| 5,501,969 | 3/1996 | Hastings et al. | 435/240.2 |
| 5,695,966 | 12/1997 | Inventi et al. | 435/78 |
| 5,786,190 | 7/1998 | Inventi et al. | 435/183 |

OTHER PUBLICATIONS

One page computer print–out of search identifying WO 9627014, "New DNA Encoding Daunorubicin 14–hydroxylase", Sep. 6, 1996 and containing abstract of application.
"Adriamycin, 14–Hydroxydauomycin, a New Antitumor Antibiotic from *S. peuceilus* var. caesius" by Arcamone, et al., *Biotechnology and Bioengineering*, vol. XI, pp. 1101–1110 (1069).
"Cloning of genetic loci involved in endoprotease activity in *Streptomyces lividans* 66: a novel neutral protease gene with an adjacent divergent putative regulatory gene", by Butler, et al., *Can J. Microbiology*, vol. 38, 1992, pp. 912–920.
"Biosynthetic relationships among daunorubicin, doxorubicin and 13–dihydrodaunorubicin in *Streptomyces peucetius*" by Crespi–Perellino, et al., *Experientia* 38 (1982), Birkhauser Verlag, CH–4010 Basel–Switzerland, pp. 1455–1456.
"A metallopretease gene from *Streptomyces coelicolor* 'Muller' and its transcriptional activator, a member of the LysR family" by Dammann, et al., *Molecular Biology*, (1992) 6(16), pp. 2267–2278.
"Isolation and Characterization of a Gene from *Streptomyces* sp. Strain C5 That Confers the Ability to Convert Daunomycin to Doxorubicin on *Streptomyces lividans* TK24" by Dickens, et al, *Journal of Bacteriology*, vol. 178, No. 11, Jun. 1996, pp. 3389–3395.
"Cloning, Sequencing, and Analysis of Aklaviketone Reductase from *Streptomyces* sp. Strain C5", by Dickens, et al., *Journal of Bacteriology*, vol. 178, No. 11, Jun. 1996, pp. 3384–3388.
"Biosynthesis of Anthracyclines in *Streptomyces Peucetius*", by Grein, et al., Sixth Int. Symp. On Actinomycetes Biology, 1985, pp. 263–266.
"Anthracyclines", Chapter 12 of *Genetics and Biochemistry of Antiobiotic Production,* edited by Leo C. Vining and Colin Struttard.
"Cloning and Sequencing of a Gene Encoding a Novel Extracellular Neutral Proteinase from *Streptomyces* sp. Strain C5 and Expression of the Gene in *Streptomyces lividans* 1326" by Lampel, et al., *Journal of Bacteriology*, vol. 174, No. 9, May 1992, pp. 2797–2808.
"Cloning and characterization of a gene encoding extracellular metalloprotease from *Streptomyces lividans*" by Lichenstein, et al., *Gene* 111 (1992), pp. 125–130.
"Microbial Metabolism of Anthracycline Antibiotics Daunomycin and Adrianycin" by Marshall, et al. *The Journal of Antibiotics,* Apr. 1978, pp. 336–342.
"Biosynthesis of Daunorubicin Glycosides" by McGuire, et al., *Antimicrobial Agents and Chemotherapy*, vol. 18, No. 3, Sep. 1980, pp. 454–464.
"Microbial Conversion of Daunomycin, Carminomycin I and Feudomycin A to Adriamycin", *Journal of Antibiotics,* vol. XXXIV No. 9, pp. 1229–1231.
"Cloning and Expression of Daunorubicin Biosynthesis Genes from *Streptomyces peucetius* and *S. peucetius* subsp. caesius" by Otten, et al., *Journal of Bacteriology*, vol. 172, No. 6, Jun. 1990, pp. 3427–3434.
"Identification of a *Saccharopolyspora erythraea* gene Required for the Final Hydroxylation Step in Erythromycin Biosynthesis" by Stassi, et al. *Journal of Bacteriology*, vol. 175, No. 1, Jan. 1993, pp. 182–189.
"Biosynthesis of Natural and Hybrid Polyketides by Anthrcycline–Producing Streptomycetes" by Strohl, et al. *Genetics and Molecular Biology of Industrial Microorganisms,* 1989 American Society for Microbiology, Washington, D.C., pp. 68–84.

(List continued on next page.)

*Primary Examiner*—Robert A. Wax
*Assistant Examiner*—Nashaat T. Nashed
*Attorney, Agent, or Firm*—Calfee, Halter & Criswold LLP

[57] ABSTRACT

The present invention provides novel methods for producing doxorubicin using daunomycin as a substrate. One method employs a genetically engineered host microorganism which is transformed with a vector, preferably a plasmid, which contains the doxA gene. Preferably, the doxA gene, also referred to herein as "doxA", is cloned into a plasmid which is then introduced into the host microorganism, preferably a bacterial host, more preferably Streptomyces, to provide a transformed host microorganism. The doxA gene, when present on a plasmid, confers on the transformed host the ability to convert daunomycin and 13-dihydrodaunomycin, to doxorubicin. The doxA gene encodes a P450-like enzyme which catalyzes the hydroxylation of daunomycin and 13-dihydrodaunomycin at C-14 to form doxorubicin; such enzyme is designated "daunomycin C-14 hydroxylase". Thus, the expression of doxA in the transformed host using a plasmid which contains doxA enables the transformed host to convert daunomycin to doxorubicin. The doxorubicin is then extracted from host microorganism cultures.

4 Claims, 21 Drawing Sheets

OTHER PUBLICATIONS

"Daunorubicin and Adramycin: Properties, Biosynthesis, and Fermentation" by White, et al., *Biotechnology of Industrial Antibiotics,* 1984, pp. 569–594.

"Isolation and Sequence Analysis of Polyketide Synthase Genes from the Caunomycin–Producing *Streptomyces* sp. Strain C5" by Ye, et al., *Journal of Bacteriology,* vol. 176, No. 20, Oct. 1994, pp. 6270–6280.

"Characterization of *Saccharopolyspora erythraea* Cytochrome P–450 Genes and Enzymens, Including 6–Deoxyerythronolide B Hydroxylase" by Andersen, et al., *Journal of Bacteriology,* vol. 174, No. 3, Feb. 1992, pp. 725–735.

Fig. 3

```
KpnI      ClaI
GGTACCCGCGCATCGATGTCATGGCCGGCAACGCCGGCGGCATGTTCTGGTCGCGCACCA          60
(orf1)..R  I  D  V  M  A  G  N  A  G  G  M  F  W  S  R  T  T CGACCCAGGACGGGTTCGAGGCCACCCTCCAGGTCAATCATCTCGCGGGCTTCCTGCTGG         120
    T  Q  D  G  F  E  A  T  L  Q  V  N  H  L  A  G  F  L  L  A CACGGCTGCTGCGGGAGCGGCTCGCGGGCGGGCGGTTGATCCTCACCTCGTCCGACGCGT         180
    R  L  L  R  E  R  L  A  G  G  R  L  I  L  T  S  S  D  A  Y ACACCCAGGGCCGGATCGACCCGGACGATCTCAACGGCGACCGTCACCGCTACAGCGCGG         240
    T  Q  G  R  I  D  P  D  D  L  N  G  D  R  H  R  Y  S  A  G GCCAGGCGTACGGCACGTCCAAACAGGCCAACATCATGACCGCCACGGAGGCCGCCCGGC         300
    Q  A  Y  G  T  S  K  Q  A  N  I  M  T  A  T  E  A  A  R  R GCTGGCCGGACGTGCTGACGGTCAGCTACCACCCCGGCGAGGTCCGCACCCGCATCGGGC         360
    W  P  D  V  L  T  V  S  Y  H  P  G  E  V  R  T  R  I  G  R GGGGCACAGTCGCCTCGACCTACTTCCGGTTCAACCCCTTCCTGCGGTCCGCGGCCAAGG         420
    G  T  V  A  S  T  Y  F  R  F  N  P  F  L  R  S  A  A  K  G GCGCCGACACTCTCGTGTGGCTGGCGGCCGCGCCGGCCGAGGAGTTGACCACGGGCGGCT         480
    A  D  T  L  V  W  L  A  A  A  P  A  E  E  L  T  T  G  G  Y ACTACAGCGACCGGCGGCTGTCCCCGGTGAGCGGCCCGACCGCCGACGCCGGCCTCGCGG         540
    Y  S  D  R  R  L  S  P  V  S  G  P  T  A  D  A  G  L  A  A CCAAGCTCTGGGAGGCCAGCGCGGCCGCCGTCGGCGACACCGCGCGCTGACCGCGGCGGG         600
    K  L  W  E  A  S  A  A  A  V  G  D  T  A  R  *

SphI                                                         660
CCTCCCCGCCCGCATGCCCGTCTCATCCGCGAGCGCAGACGCTCGTGTGCCGATCCGTCG rbs                                                                  720
AAAGGAACGATTCGTGACCAGGTTCGCGCCCGGCGCCCCCGCATGGTTCGACCTCGGGTC
      (orfA) fM  T  R  F  A  P  G  A  P  A  W  F  D  L  G  S GCCCGATGTCGCCGCCTCGGCCGACTTCTACACCGGCCTCTTCGGCTGGACCGCGACCGT         780
    P  D  V  A  A  S  A  D  F  Y  T  G  L  F  G  W  T  A  T  V GCCCGATGTCGCCGCCTCGGCCGACTTCTACACCGGCCTCTTCGGCTGGACCGCGACCGT         840
    P  D  V  A  A  S  A  D  F  Y  T  G  L  F  G  W  T  A  T  V
```

Fig. 3 (con't)

```
CGCGGTCGCCCGCCATCAGATCGACACGCCCTACCACCGTCCGTACGGGCCCGGCAACGA    900
 A  V  A  R  H  Q  I  D  T  P  Y  H  R  P  Y  G  P  G  N  D

SphI                                               960
CCAGCACGGCATGCCGGCCATCTGGACCGTGTACTTCGCCACCAACGACGCCGACGCACT
 Q  H  G  M  P  A  I  W  T  V  Y  F  A  T  N  D  A  D  A  L

GACCAAACGGGTCGAGACGGCGGGTGGCGACGTCATCATGACCCCGATGGACGTCCTCGG   1020
 T  K  R  V  E  T  A  G  G  D  V  I  M  T  P  M  D  V  L  G

TCTCGGCCGGATGGCGGTCTTCGCCGACCCATCGGGGGCCGCGTTCGCGGTGTGGCGCAA   1080
 L  G  R  M  A  V  F  A  D  P  S  G  A  A  F  A  V  W  R  K

GGGCGTCATGGAGGGCGCGGAGGTGACGGGCGTGCCCGGCTCGGTCGGCTGGGTGGAACT   1140
 G  V  M  E  G  A  E  V  T  G  V  P  G  S  V  G  W  V  E  L

GGTGACCGACGACATCGGGACCGCCCGTGGCTTCTACCGTGCGACCCTCGGCCTGGCTCC   1200
 V  T  D  D  I  G  T  A  R  G  F  Y  R  A  T  L  G  L  A  P

GGCCGACACCGGACGCAAGGGCGTCACCGACCCGGTTTGGCACATCCATGACACACCGGT   1260
 A  D  T  G  R  K  G  V  T  D  P  V  W  H  I  H  D  T  P  V

CGCCGGCACCCGGGAACTGGGCACGACCGGCGCGGTACGGCCCCACTGGGCCGTGCTGTT   1320
 A  G  T  R  E  L  G  T  T  G  A  V  R  P  H  W  A  V  L  F

CTCCGTGCACGACTGCGACGCGACGGTCCGGCGGGCCGTCGAACTCGGCGGCTCCGTCGA   1380
 S  V  H  D  C  D  A  T  V  R  R  A  V  E  L  G  G  S  V  E

SalI                                              1440
GAACGAGCCCGTCGACACCCCCAGGGGGCGGCGGGCGGACCTGCTCGACCCGCACGGGGC
 N  E  P  V  D  T  P  R  G  R  R  A  D  L  L  D  P  H  G  A

CGGCTTCTCGGTGGTCGAACTGCGGGAGGCGTACCCCGCGGCGGCGGACGGTGCCTCATG   1500
 G  F  S  V  V  E  L  R  E  A  Y  P  A  A  A  D  G  A  S  *
                                            (doxA)       fM SalI                                              1560
AGCGGCGAGGCGCCGCGGGTGGCCGTCGACCCGTTCTCGTGTCCCATGATGACCATGCAG
 S  G  E  A  P  R  V  A  V  D  P  F  S  C  P  M  M  T  M  Q CGCAAACCCGAGGTGCACGACGCATTCCGAGAGGCGGGCCCCGTCGTCGAGGTGAACGCC   1620
 R  K  P  E  V  H  D  A  F  R  E  A  G  P  V  V  E  V  N  A CCCGCGGGCGGACCCGCCTGGGTCATCACCGATGACGCCCTCGCCCGCGAGGTGCTGGCC   1680
 P  A  G  G  P  A  W  V  I  T  D  D  A  L  A  R  E  V  L  A
```

Fig. 3 (con't)

```
GATCCCCGGTTCGTGAAGGACCCCGATCTCGCGCCCACCGCCTGGCGGGGGTGGACGAC    1740
 D   P   R   F   V   K   D   P   D   L   A   P   T   A   W   R   G   V   D   D

BspEI                                                        1800
GGTCTCGACATCCCCGTTCCGGAGCTGCGTCCGTTCACGCTCATCGCCGTGGACGGTGAG
 G   L   D   I   P   V   P   E   L   R   P   F   T   L   I   A   V   D   G   E

GACCACCGGCGTCTGCGCCGCATCCACGCACCGGCGTTCAACCCGCGCCGGCTGGCCGAG    1860
 D   H   R   R   L   R   R   I   H   A   P   A   F   N   P   R   R   L   A   E

CGGACGGATCGCATCGCCGCCATCGCCGACCGGCTGCTCACCGAACTCGCCGACTCCTCC    1920
 R   T   D   R   I   A   A   I   A   D   R   L   L   T   E   L   A   D   S   S

GACCGGTCGGGCGAACCGGCCGAGCTGATCGGCGGCTTCGCGTACCACTTCCCGCTGTTG    1980
 D   R   S   G   E   P   A   E   L   I   G   G   F   A   Y   H   F   P   L   L

GTCATCTGCGAACTGCTCGGCGTGCCGGTCACCGATCCGGCAATGGCCCGCGAGGCCGTC    2040
 V   I   C   E   L   L   G   V   P   V   T   D   P   A   M   A   R   E   A   V

GGCGTGCTCAAGGCACTCGGCCTCGGCGGCCCGCAGAGCGCCGGCGGTGACGGCACGGAC    2100
 G   V   L   K   A   L   G   L   G   G   P   Q   S   A   G   G   D   G   T   D

CCTGCCGGGGACGTGCCGGACACGTCGGCGCTGGAGAGCCTTCTCCTCGAAGCCGTGCAC    2160
 P   A   G   D   V   P   D   T   S   A   L   E   S   L   L   L   E   A   V   H

GCGGCCCGGCGGAAAGACACCCGGACCATGACCCGCGTGCTCTATGAACGCGCACAGGCA    2220
 A   A   R   R   K   D   T   R   T   M   T   R   V   L   Y   E   R   A   Q   A

BclI                                               2280
GAGTTCGGCTCGGTCTCCGACGACCAGCTCGTCTACATGATCACCGGACTCATCTTCGCC
 E   F   G   S   V   S   D   D   Q   L   V   Y   M   I   T   G   L   I   F   A

GGCCACGACACCACCGGCTCGTTCCTGGGCTTCCTGCTTGCGGAGGTCCTGGCGGGCCGT    2340
 G   H   D   T   T   G   S   F   L   G   F   L   L   A   E   V   L   A   G   R

CTCGCGGCGGACGCCGACGGGGACGCCATCTCCCGGTTCGTGGAGGAGGCGCTGCGCCAC    2400
 L   A   A   D   A   D   G   D   A   I   S   R   F   V   E   E   A   L   R   H

CACCCGCCGGTGCCCTACACGTTGTGGAGGTTCGCTGCCACGGAGGTGGTCATCCGCGGT    2460
 H   P   P   V   P   Y   T   L   W   R   F   A   A   T   E   V   V   I   R   G

GTCCGGCTGCCCCGCGGAGCGCCGGTACTGGTGGACATCGAGGGCACCAACACCGACGGC    2520
 V   R   L   P   R   G   A   P   V   L   V   D   I   E   G   T   N   T   D   G
```

Fig. 3 (con't)

```
CGCCATCACGACGCCCCGCACGCTTTCCACCCGGACCGCCCTTCGAGGCGGCGGCTCACC    2580
 R  H  H  D  A  P  H  A  F  H  P  D  R  P  S  R  R  R  L  T

PvuII                 2640
TTCGGCGACGGGCCGCACTACTGCATCGGGGAGCAGCTCGCCCAGCTGGAATCGCGCACG
 F  G  D  G  P  H  Y  C  I  G  E  Q  L  A  Q  L  E  S  R  T

ATGATCGGCGTACTGCGCAGCAGGTTCCCCCAAGCCCGACTGGCCGTGCCGTACGAGGAG    2700
 M  I  G  V  L  R  S  R  F  P  Q  A  R  L  A  V  P  Y  E  E

TTGCGGTGGTGCAGGAAGGGGGCCCAGACAGCGCGGCTCACTGACCTGCCCGTCTGGCTG    2760
 L  R  W  C  R  K  G  A  Q  T  A  R  L  T  D  L  P  V  W  L

CGTTGATGGGCCGACCGCGACCCGGCACGGGACCGCCCACCGCCCATCGCGCGGTGGGCG    2820
 R  *

GTCCCGTGCCGGTCGCCCGGTGCGGTCCTCTCCCGACGCTCGCTCCCCCTGTGACTTTCT    2880

CACATCGAGACGTGACGAAATAATCCCAGCAAGTGCCATGCACACTTTCATGGCGGACAT    2940

TCACTTGCGAGGATGGAGTGAGCACACGGGGCCGCCCGAGACACCCTACGGCCGCCGGAA    3000 rbs                       3060
GTATGCCACCTGTTGACGCGAATGGAACGCCACAGAGGGAGCACCGGCAATGCAGATCAA
                                      (dauI)    fM  Q  I  N TATGTTGGGCCCGCTCGTTGCACATCACAATGGCACGTCGGTGACCCCGATAGCCAGAAA    3120
 M  L  G  P  L  V  A  H  H  N  G  T  S  V  T  P  I  A  R  K ACCCCGGCAGGTATTCTCACTGCTCGCTCTTCAGGCAGGAACCGTCGTTCCGGTCCCCGC    3180
 P  R  Q  V  F  S  L  L  A  L  Q  A  G  T  V  V  P  V  P  A SstI                                                      3196
GCTGATGGAGGAGCTC
 L  M  E  E  L...
```

Fig. 6

Sequence of activator gene *snp* and daunomycin C-14 hydroxyl gene *doxA* in pANT195

```
      KpnI
  gcaggcGGTACCGCCGACCCGCTGCATCCCCCGCACCGCCGTCCCCCCCAGGGCATCTC
3'-ccgCCATGGCGGCTGGGCGACGTAGGGGGCGTGGCGGCAGGGGGGGTCCCGTAGAG       60

CCGTCGGGTTACGGGAAGGGGGCCGGGGTACGCGGTCGTCACGGGAGGGCTGGGACGAGT
  GGCAGCCCAATGCCCTTCCCCCGGCCCCATGCGCCAGCAGTGCCCTCCCGACCCTGCTCA      120
                                        *    P  L  A  P  V  L

GCCCCCGACCCACTGCGTTCCAGCCACTCCCGGTACGCCGGGGCCTGCCGGGCGACCTCC
  CGGGGGCTGGGTGACGCAAGGTCGGTGAGGGCCATGCGGCCCCGGACGGCCCGCTGGAGG      180
   A  G  S  G  S  R  E  L  W  E  R  Y  A  P  A  Q  R  A  V  E

StuI
  CCGTAGGCCTCCGCGAGGTCGGGGTAGACGCCCTCCAGTTCCGTGTCCGTGCGGGCCGCC
  GGCATCCGGAGGCGCTCCAGCCCCATCTGCGGGAGGTCAAGGCACAGGCACGCCCGGCGG      240
   G  Y  A  E  A  L  D  P  Y  V  G  E  L  E  T  D  T  R  A  A

AGCAGCAGCCGTACGCCGAGCGGGTCGCCGTGCAGCCGGCGGACGGCCGTCTCGGCGCGG
  TCGTCGTCGGCATGCGGCTCGCCCAGCGGCACGTCGGCCGCCTGCCGGCAGAGCCGCGCC      300
   L  L  L  R  V  G  L  P  D  G  H  L  R  R  V  A  T  E  A  R

GAGGGCGAGGTCGGCTGGACCACGGTGACGACCTCGCCGGTGGCGACCAGGTACGCGGCG
  CTCCCGCTCCAGCCGACCTGGTGCCACTGCTGGAGCGGCCACCGCTGGTCCATGCGCCGC      360
   S  P  S  T  P  Q  V  V  T  V  V  E  G  T  A  V  L  Y  A  A

GAGTGGTAGTCCCCGTGCAGGATGCGCGAGTCGAGTCCCTCGGCGCGCAGGACCCGGCGC
  CTCACCATCAGGGGCACGTCCTACGCGCTCAGCTCAGGGAGCCGCGCGTCCTGGGCCGCG      420
   S  H  Y  D  G  H  L  I  R  S  D  L  G  E  A  R  L  V  R  R

ACCGCGTTCCACTCGCCGTCGACGGTGGGGTCGATCATCCAGCGGGTCGTGGGCCAGGTC
  TGGCGCAAGGTGAGCGGCAGCTGCCACCCCAGCTAGTAGGTCGCCCAGCACCCGGTCCAG      480
   V  A  N  W  E  G  D  V  T  P  D  I  M  W  R  T  T  P  W  T

GGCGAGGCGTACGACGTGGCTTCGGCGGCCGGGTGGTCGGCCGGCAGGCAGACGAACTGC
  CCGCTCCGCATGCTGCACCGAAGCCGCCGGCCCACCAGCCGGCCGTCCGTCTGCTTGACG      540
   P  S  A  Y  S  T  A  E  A  A  P  H  D  A  P  L  C  V  F  Q

GGTTCCCGCTGGACCAGTACGCGGACCCGGAGCCCTTCGGGGACGCGCAGGCTGCCCTCG
  CCAAGGGCGACCTGGTCATGCGCCTGGGCCTCGGGAAGCCCCTGCGCGTCCGACGGGAGC      600
   P  E  R  Q  V  L  V  R  V  R  L  G  E  P  V  R  L  S  G  E
```

Fig. 6 (con't)

```
ACCTCGTGCACGAAGGCGACGTCGAGGTGGCCGTCGGCCACCATGCGCAGCAGGGCGTTG
TGGAGCACGTGCTTCCGCTGCAGCTCCACCGGCAGCCGGTGGTACGCGTCGTCCCGCAAC      660
 V  E  H  V  F  A  V  D  L  H  G  D  A  V  M  R  L  L  A  N

GCGGAGACGTCCATGTGCAGGGTGGGTTCCTGCCAGTGCCGGAGCCGGCGCAGCCAGCCC
CGCCTCTGCAGGTACACGTCCCACCCAAGGACGGTCACGGCCTCGGCCGCGTCGGTCGGG      720
 A  S  V  D  M  H  L  T  P  E  Q  W  H  R  L  R  R  L  W  G

GCCAGGGCCCGGCTGGCCGTGGAGCCGACGCGCAGGCTGGCGTCCGCGACGGCGGCGGCG
CGGTCCCGGGCCGACCGGCACCTCGGCTGCGCGTCCGACCGCAGGCGCTGCCGCCGCCGC      780
 A  L  A  R  S  A  T  S  G  V  R  L  S  A  D  A  V  A  A  A

CGGGCCTCGCTGACGAGGGAGCACAATTCGGCCACCAGGGGGCGGGCACGACTGAGCACC
GCCCGGAGCGACTGCTCCCTCGTGTTAAGCCGGTGGTCCCCCGCCCGTGCTGACTCGTGG      840
 R  A  E  S  V  L  S  C  L  E  A  V  L  P  R  A  R  S  L  V

AGCCGGCCCAGCGGTGTGGGGCGGCAGCCGGTGCGGGCCCGGACGAACAGGGCACCGCCC
TCGGCCGGGTCGCCACACCCCGCCGTCGGCCACGCCCGGGCCTGCTTGTCCCGTGGCGGG      900
 L  R  G  L  P  T  P  R  C  G  T  R  A  R  V  F  L  A  G  G

PvuII
AGCTCGTGTTCGATGCGCCGCAGCTGCGTGCTCAACGAGGGCTGTGTCACTCCCAGTTGG
TCGAGCACAAGCTACGCGGCGTCGACGCACGAGTTGCTCCCGACACAGTGAGGGTCAACC      960
 L  E  H  E  I  R  R  L  Q  T  S  L  S  P  Q  T  V  G  L  Q
                    α-Helix-ß-Turn-α-Helix:  DNA-Binding SauI
CGTGCCGCGCGGTGCAGGCTGCCGGTGTCGGCGATGGCGCACAGCGCCCTGAGGTGCCTG
GCACGGCGCGCCACGTCCGACGGCCACAGCCGCTACCGCGTGTCGCGGGACTCCACGGAC      1020
 R  A  A  R  H  L  S  G  T  D  A  I  A  C  L  A  R  L  H  R
     Domain ACCTCAAGCTCCATGTCCTGGGAGGGTAAGGCGGAAGTTCAGCTTTCACCAGACATACAA
TGGAGTTCGAGGTACAGGACCCTCCCATTCCGCCTTCAAGTCGAAAGTGGTCTGTATG-5'   1080
 V  E  L  E  fM  ←       -10?                      -35?
         Proposed tsp??

AATGGCGACCGATCAGGACCATCGGGCCTTCACGGCGCGAGGCGTCGGCCCGGATCGGCA      1140

Proposed SnpR
                                                 ──→             1200
GGGGCCCCGGCCGGGGCCGCCGGGCAGGGCGGGGCAGGTGGGGACGGAGGGGGATAGGGC
```

Fig. 6 (con't)

```
binding site
←―――――            -35?              -10?
GGCCCTATCGGCGGTTGCCATCATCACAACGGCCGTACGGGCACGGACACTCACGATGTC    1260

Proposed
tsp          XhoI RBS   ClaI    SphI   RBS
TGACTCATCCCCCCACCTCGAGGAGTCATCGATGCGCATGCGGAGGGGTGCCTCATGAGC    1320
                                                    →fM S
                     (fm r  m  r  r  g  a  s  *)

GGCGAGGCGCCGCGGGTGGCCGTCGACCCGTTCTCGTGTCCCATGATGACCATGCAGCGC
 G   E   A   P   R   V   A   V   D   P   F   S   C   P   M   M   T   M   Q   R    1380

AAACCCGAGGTGCACGACGCATTCCGAGAGGCGGGCCCCGTCGTCGAGGTGAACGCCCCC
 K   P   E   V   H   D   A   F   R   E   A   G   P   V   V   E   V   N   A   P    1440

GCGGGCGGACCCGCCTGGGTCATCACCGATGACGCCCTCGCCCGCGAGGTGCTGGCCGAT
 A   G   G   P   A   W   V   I   T   D   D   A   L   A   R   E   V   L   A   D    1500

CCCCGGTTCGTGAAGGACCCCGATCTCGCGCCCACCGCCTGGCGGGGGGTGGACGACGGT
 P   R   F   V   K   D   P   D   L   A   P   T   A   W   R   G   V   D   D   G    1560

BspEI
CTCGACATCCCCGTTCCGGAGCTGCGTCCGTTCACGCTCATCGCCGTGGACGGTGAGGAC
 L   D   I   P   V   P   E   L   R   P   F   T   L   I   A   V   D   G   E   D    1620

CACCGGCGTCTGCGCCGCATCCACGCACCGGCGTTCAACCCGCGCCGGCTGGCCGAGCGG
 H   R   R   L   R   R   I   H   A   P   A   F   N   P   R   R   L   A   E   R    1680

ACGGATCGCATCGCCGCCATCGCCGACCGGCTGCTCACCGAACTCGCCGACTCCTCCGAC
 T   D   R   I   A   A   I   A   D   R   L   L   T   E   L   A   D   S   S   D    1740

CGGTCGGGCGAACCGGCCGAGCTGATCGGCGGCTTCGCGTACCACTTCCCGCTGTTGGTC
 R   S   G   E   P   A   E   L   I   G   G   F   A   Y   H   F   P   L   L   V    1800

ATCTGCGAACTGCTCGGCGTGCCGGTCACCGATCCGGCAATGGCCCGCGAGGCCGTCGGC
 I   C   E   L   L   G   V   P   V   T   D   P   A   M   A   R   E   A   V   G    1860

GTGCTCAAGGCACTCGGCCTCGGCGGCCCGCAGAGCGCCGGCGGTGACGGCACGGACCCT
 V   L   K   A   L   G   L   G   G   P   Q   S   A   G   D   G   T   D   P        1920
```

Fig. 6 (con't)

```
GCCGGGGACGTGCCGGACACGTCGGCGCTGGAGAGCCTTCTCCTCGAAGCCGTGCACGCG
 A  G  D  V  P  D  T  S  A  L  E  S  L  L  L  E  A  V  H  A           1980

GCCCGGCGGAAAGACACCCGGACCATGACCCGCGTGCTCTATGAACGCGCACAGGCAGAG
 A  R  R  K  D  T  R  T  M  T  R  V  L  Y  E  R  A  Q  A  E           2040

TTCGGCTCGGTCTCCGACGACCAGCTCGTCTACATGATCACCGGACTCATCTTCGCCGGC
 F  G  S  V  S  D  D  Q  L  V  Y  M  I  T  G  L  I  F  A  G           2100

CACGACACCACCGGCTCGTTCCTGGGCTTCCTGCTTGCGGAGGTCCTGGCGGGCCGTCTC
 H  D  T  T  G  S  F  L  G  F  L  L  A  E  V  L  A  G  R  L           2160

GCGGCGGACGCCGACGGGGACGCCATCTCCCGGTTCGTGGAGGAGGCGCTGCGCCACCAC
 A  A  D  A  D  G  D  A  I  S  R  F  V  E  E  A  L  R  H  H           2220

CCGCCGGTGCCCTACACGTTGTGGAGGTTCGCTGCCACGGAGGTGGTCATCCGCGGTGTC
 P  P  V  P  Y  T  L  W  R  F  A  A  T  E  V  V  I  R  G  V           2280

CGGCTGCCCCGCGGAGCGCCGGTACTGGTGGACATCGAGGGCACCAACACCGACGGCCGC
 R  L  P  R  G  A  P  V  L  V  D  I  E  G  T  N  T  D  G  R           2340

CATCACGACGCCCCGCACGCTTTCCACCCGGACCGCCCTTCGAGGCGGCGGCTCACCTTC
 H  H  D  A  P  H  A  F  H  P  D  R  P  S  R  R  R  L  T  F           2400

GGCGACGGGCCGCACTACTGCATCGGGGAGCAGCTCGCCCAGCTGGAATCGCGCACGATG
 G  D  G  P  H  Y  C  I  G  E  Q  L  A  Q  L  E  S  R  T  M           2460

ATCGGCGTACTGCGCAGCAGGTTCCCCCAAGCCCGACTGGCCGTGCCGTACGAGGAGTTG
 I  G  V  L  R  S  R  F  P  Q  A  R  L  A  V  P  Y  E  E  L           2520

CGGTGGTGCAGGAAGGGGGCCCAGACAGCGCGGCTCACTGACCTGCCCGTCTGGCTGCGT
 R  W  C  R  K  G  A  Q  T  A  R  L  T  D  L  P  V  W  L  R           2580

TGATGGGCCGACCGCGACCCGGCACGGGACCGCCCACCGCCCATCGCGCGGTGGGCGGTC
 *                                                                    2640

CCGTGCCGGTCGCCCGGTGCGGTCCTCTCCCGACGCTCGCTCCCCCTGTGACTTTCTCAC         2700

ATCGAGACGTGACGAAATAATCCCAGCAAGTGCCATGCACACTTTCATGGCGGACATTCA         2760
```

Fig. 6 (con't)

```
CTTGCGAGGATGGAGTGAGCACACGGGGCCGCCCGAGACACCCTACGGCCGCCGGAAGTA                    2820 rbs
TGCCACCTGTTGACGCGAATGGAACGCCACAGAGGGAGCACCGGCAATGCAGATCAATAT                    2880
                                    (dauI)    fM  Q   I   N   M GTTGGGCCCGCTCGTTGCACATCACAATGGCACGTCGGTGACCCCGATAGCCAGAAAACC
 L   G   P   L   V   A   H   H   N   G   T   S   V   T   P   I   A   R   K   P  2940

CCGGCAGGTATTCTCACTGCTCGCTCTTCAGGCAGGAACCGTCGTTCCGGTCCCCGCGCT
 R   Q   V   F   S   L   L   A   L   Q   A   G   T   V   V   P   V   P   A   L  3000

SstI
GATGGAGGAGCTC                                                                   3013
 M   E   E   L . . .
```

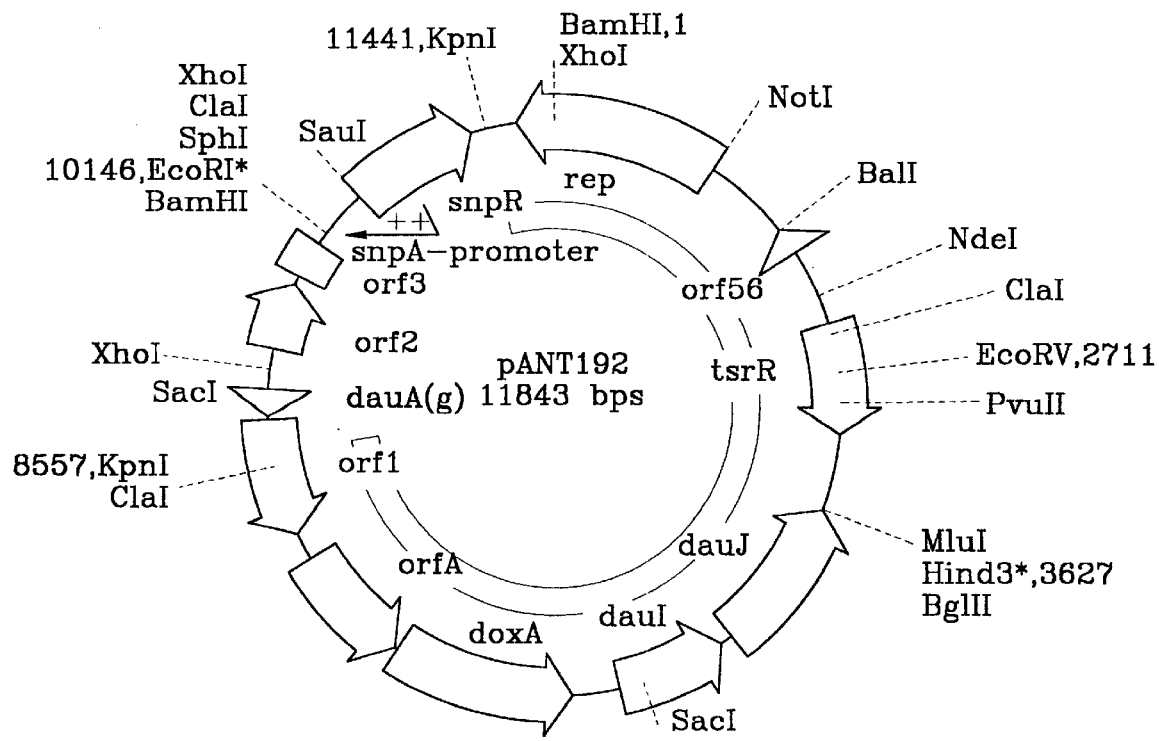
(Open box indicates sequence in pANT194)
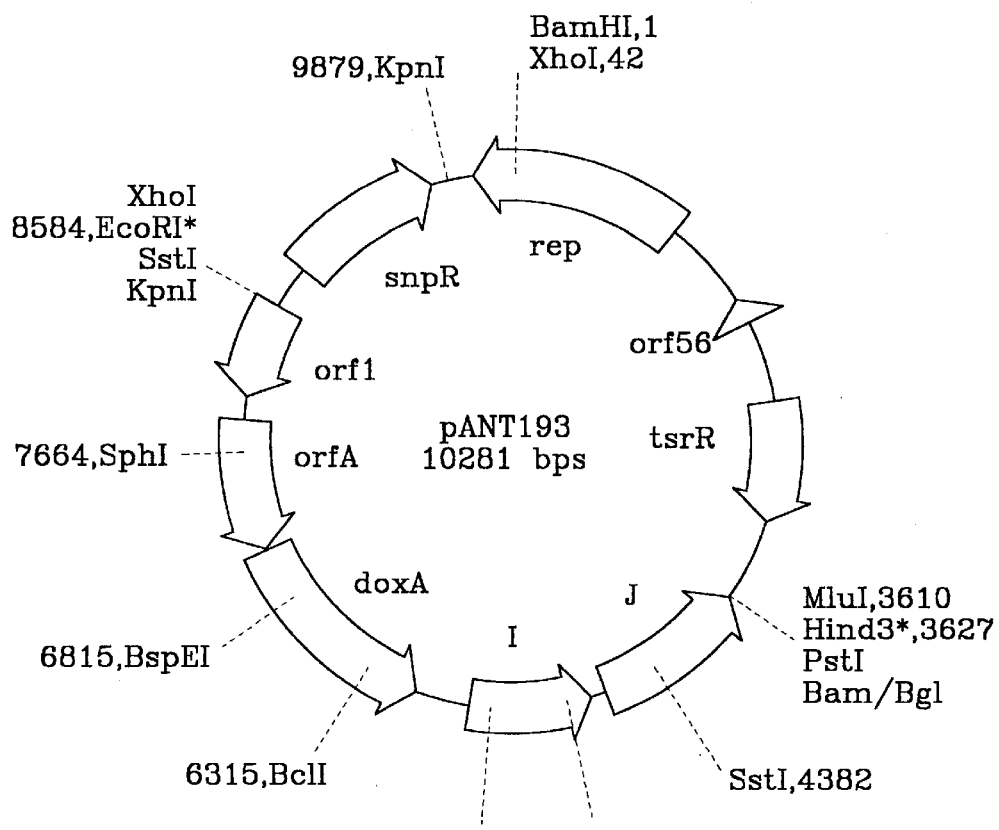
Fig.7

FIG. 9

```
      -35                    -10              lac operator
TGTTGACAATTAATCATCCGGCTCGTATAATGTGTGGAATTGTGAGCGGATAACAATTTC    60 rrnB antiterminator
ACACAGGAAACAGCGCCGCTGAGAAAAAGCGAAGCGGCACTGCTCTTTAACAATTTATCA   120 g10 translational enhancer
GACAATCTGTGTGGGCACTCGACCGGAATTGGGCATCGATTAACTTTATTATTAAAAATT   180 rbs             Mini cistron
AAAGAGGTATATATTAATGTATCGATTAAATAAGGAGGAATAAACCATGGGGGGTTCTCA   240
               fm  Y  R  L  N  K  E  E  *    fm G  G  S TCATCATCATCATCATGGTATGGCTAGCATGACTGGTGGACAGCAAATGGGTCGGGATCT   300
 H  H  H  H  H  H  G  M  A  S  M  T  G  G  Q  Q  M  G  R  D GTACGACGATGACGATAAGG                                           320
 L  Y  D  D  D  D  K↑
Enterokinase cleavage site BglII
    BamHI    XhoI    PstI     KpnI       EcoRI
ATCGATGGATCCGACCTCGAGATCTGCAGATGGTACCATATGGGAATTCGGAGGGGTGCC
 D  R  W  I  R  P  R  D  L  Q  M  V  P  Y  G  N  S  E  G  C TCATGAGCGGCGAGGCGCCG. . .
 L  M  S  G  E  A  P. . .
    Native DoxA sequence
```

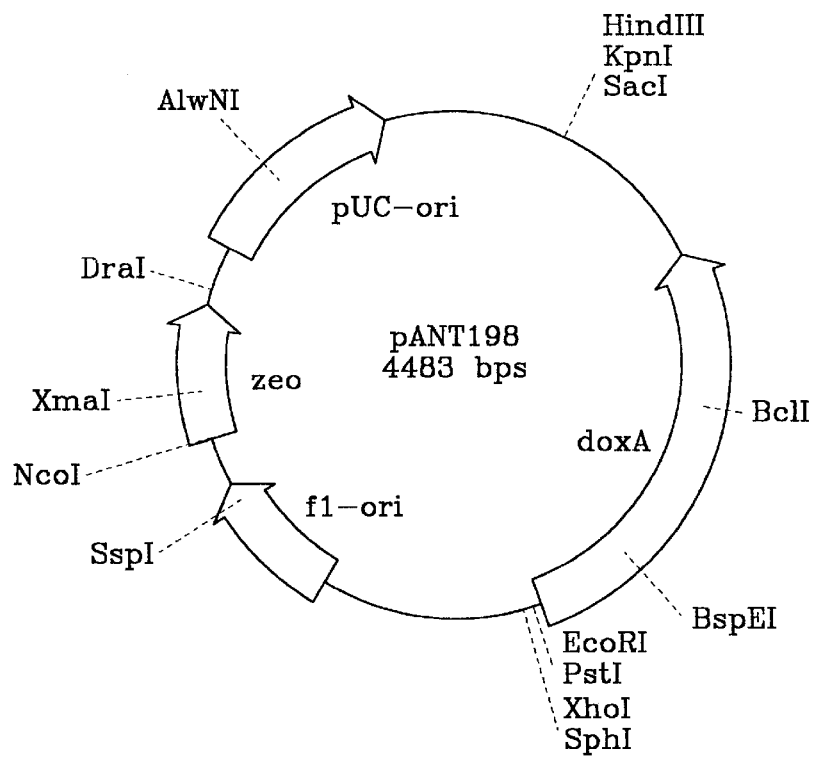
pANT199 — doxA in pTrcHis for Expression
as a Fusion Protein in Escherichia coli
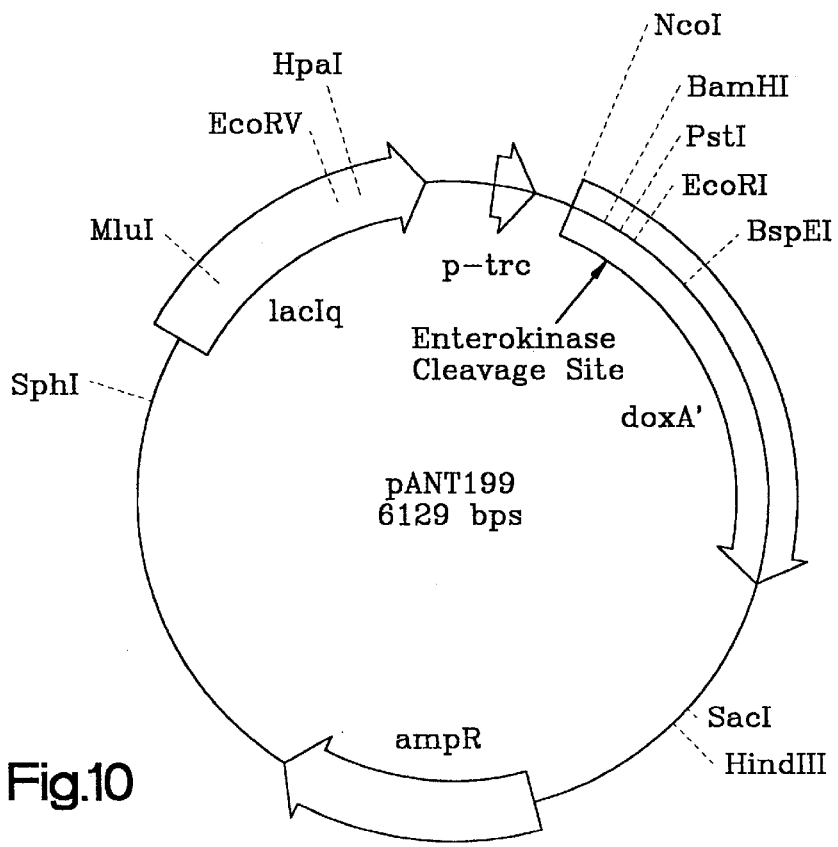
Fig.10

Fig. 11

```
    PstI
    CTGCAGCTCGCCCGGCCGCCGGTCCCCCTGCCGTCCGGCCCGTCCCAGAGGCAGCGT          57

CGGCGGCTCCTGCCTCCCCCGCCCGGCGCCGACCGGGACCCGCAAACCCCTTGATCCGCT          117

BclI
GTCGGGGGTGATCACGTCAGTTTTCGCACGTGAGCCACGCCACCGGCGGGGCGCACCCGC          177

DNA region responsible for
GCCAAAGACCACCGGAAGGGACGTCCGCTCGGAAAGGAATTGCCCCTTCCGCCCGTCGGC          237

"activation" of melC1-p
GAGGACCGCCGCGAGCAAGATCATCTTTGTTCAACATTGCACGACAGATCATTAATTGTC          297

CGGATCGCGGCCAACCGGTCCGGGCCGATTTCTCCCCTTCTCCTCCGGTCGATAGGTATG          357 melC1-p
       **→→→→→                  rbs       SphI     rbs
CGGGGTCGTCAACCCAACGCACCCCAGGAGGTCCCGCATGCGGAGGGGTGCCTCATGAGC          417
                                              (doxA)   →fM  S
                          (oligopeptide)    (fm  r  r  g  a  s  *)

SalI
GGCGAGGCGCCGCGGGTGGCCGTCGACCCGTTCTCGTGTCCCATGATGACCATGCAGCGC          477
 G   E   A   P   R   V   A   V   D   P   F   S   C   P   M   M   T   M   Q   R

AAACCCGAGGTGCACGACGCATTCCGAGAGGCGGGCCCCGTCGTCGAGGTGAACGCCCCC
 K   P   E   V   H   D   A   F   R   E   A   G   P   V   V   E   V   N   A   P          537

GCGGGCGGACCCGCCTGGGTCATCACCGATGACGCCCTCGCCCGCGAGGTGCTGGCCGAT
 A   G   G   P   A   W   V   I   T   D   D   A   L   A   R   E   V   L   A   D          597

CCCCGGTTCGTGAAGGACCCCGATCTCGCGCCCACCGCCTGGCGGGGGGTGGACGACGGT
 P   R   F   V   K   D   P   D   L   A   P   T   A   W   R   G   V   D   D   G          657

BspEI
CTCGACATCCCCGTTCCGGAGCTGCGTCCGTTCACGCTCATCGCCGTGGACGGTGAGGAC          717
 L   D   I   P   V   P   E   L   R   P   F   T   L   I   A   V   D   G   E   D
```

Fig. 11 (con't)

```
CACCGGCGTCTGCGCCGCATCCACGCACCGGCGTTCAACCCGCGCCGGCTGGCCGAGCGG
 H  R  R  L  R  R  I  H  A  P  A  F  N  P  R  R  L  A  E  R      777

ACGGATCGCATCGCCGCCATCGCCGACCGGCTGCTCACCGAACTCGCCGACTCCTCCGAC
 T  D  R  I  A  A  I  A  D  R  L  L  T  E  L  A  D  S  S  D      837

CGGTCGGGCGAACCGGCCGAGCTGATCGGCGGCTTCGCGTACCACTTCCCGCTGTTGGTC
 R  S  G  E  P  A  E  L  I  G  G  F  A  Y  H  F  P  L  L  V      897

ATCTGCGAACTGCTCGGCGTGCCGGTCACCGATCCGGCAATGGCCCGCGAGGCCGTCGGC
 I  C  E  L  L  G  V  P  V  T  D  P  A  M  A  R  E  A  V  G      957

GTGCTCAAGGCACTCGGCCTCGGCGGCCCGCAGAGCGCCGGCGGTGACGGCACGGACCCT
 V  L  K  A  L  G  L  G  G  P  Q  S  A  G  G  D  G  T  D  P     1017

GCCGGGGACGTGCCGGACACGTCGGCGCTGGAGAGCCTTCTCCTCGAAGCCGTGCACGCG
 A  G  D  V  P  D  T  S  A  L  E  S  L  L  L  E  A  V  H  A     1077

GCCCGGCGGAAAGACACCCGGACCATGACCCGCGTGCTCTATGAACGCGCACAGGCAGAG
 A  R  R  K  D  T  R  T  M  T  R  V  L  Y  E  R  A  Q  A  E     1137

TTCGGCTCGGTCTCCGACGACCAGCTCGTCTACATGATCACCGGACTCATCTTCGCCGGC
 F  G  S  V  S  D  D  Q  L  V  Y  M  I  T  G  L  I  F  A  G     1197

CACGACACCACCGGCTCGTTCCTGGGCTTCCTGCTTGCGGAGGTCCTGGCGGGCCGTCTC
 H  D  T  T  G  S  F  L  G  F  L  L  A  E  V  L  A  G  R  L     1257

GCGGCGGACGCCGACGGGGACGCCATCTCCCGGTTCGTGGAGGAGGCGCTGCGCCACCAC
 A  A  D  A  D  G  D  A  I  S  R  F  V  E  E  A  L  R  H  H     1317

CCGCCGGTGCCCTACACGTTGTGGAGGTTCGCTGCCACGGAGGTGGTCATCCGCGGTGTC
 P  P  V  P  Y  T  L  W  R  F  A  A  T  E  V  V  I  R  G  V     1377

CGGCTGCCCCGCGGAGCGCCGGTACTGGTGGACATCGAGGGCACCAACACCGACGGCCGC
 R  L  P  R  G  A  P  V  L  V  D  I  E  G  T  N  T  D  G  R     1437

CATCACGACGCCCCGCACGCTTTCCACCCGGACCGCCCTTCGAGGCGGCGGCTCACCTTC
 H  H  D  A  P  H  A  F  H  P  D  R  P  S  R  R  R  L  T  F     1497

GGCGACGGGCCGCACTACTGCATCGGGGAGCAGCTCGCCCAGCTGGAATCGCGCACGATG
 G  D  G  P  H  Y  C  I  G  E  Q  L  A  Q  L  E  S  R  T  M     1557
```

Fig. 11 (con't)

```
GGCGACGGGCCGCACTACTGCATCGGGGAGCAGCTCGCCCAGCTGGAATCGCGCACGATG
 G   D   G   P   H   Y   C   I   G   E   Q   L   A   Q   L   E   S   R   T   M          1617

CGGTGGTGCAGGAAGGGGGCCCAGACAGCGCGGCTCACTGACCTGCCCGTCTGGCTGCGT
 R   W   C   R   K   G   A   Q   T   A   R   L   T   D   L   P   V   W   L   R          1677

TGATGGGCCGACCGCGACCCGGCACGGGACCGCCCACCGCCCATCGCGCGGTGGGCGGTC
 *                                                                                      1737

CCGTGCCGGTCGCCCGGTGCGGTCCTCTCCCGACGCTCGCTCCCCCTGTGACTTTCTCAC          1797

ATCGAGACGTGACGAAATAATCCCAGCAAGTGCCATGCACACTTTCATGGCGGACATTCA          1857

CTTGCGAGGATGGAGTGAGCACACGGGGCCGCCCGAGACACCCTACGGCCGCCGGAAGTA          1917 rbs
TGCCACCTGTTGACGCGAATGGAACGCCACAGAGGGAGCACCGGCAATGCAGATCAATAT          1977
                                      (dauI)    fM  Q   I   N   M GTTGGGCCCGCTCGTTGCACATCACAATGGCACGTCGGTGACCCCGATAGCCAGAAAACC
 L   G   P   L   V   A   H   H   N   G   T   S   V   T   P   I   A   R   K   P          2037

CCGGCAGGTATTCTCACTGCTCGCTCTTCAGGCAGGAACCGTCGTTCCGGTCCCCGCGCT
 R   Q   V   F   S   L   L   A   L   Q   A   G   T   V   V ·P   V   P   A   L          2097

SstI
GATGGAGGAGCTC                                                                           2110
 M   E   E   L...
```

METHODS OF PRODUCING DOXORUBICIN

CROSS-REFERENCE TO RELATED APPLICATIONS

This application is a divisional of the following commonly assigned, copending U.S. Pat. application Ser. No. 08/653,650, filed May 14, 1996.

BACKGROUND OF THE INVENTION

Daunomycin and doxorubicin are clinically important chemotherapeutic agents. Daunomycin is used primarily to treat adult myelogenous leukemia. Doxorubicin is widely used to treat a variety of neoplasias, making it the more valuable of the two anticancer drugs. The world wide market for doxorubicin is estimated to exceed $156 million. As of 1984, the wholesale price for doxorubicin was estimated to be $1,370,000 per kilogram.

While daunomycin is synthesized by several species of Streptomyces, doxorubicin is biologically synthesized by only one strain, a mutant strain of *Streptomyces peucetius*, called *S. peucetius* subsp. *caesius* which is available from the American Type Culture Collection under Accession number 27952.

The alternative in vitro laboratory synthesis of doxorubicin is difficult. The in vitro synthesis of doxorubicin is a process involving multiple steps and resulting in a poor yield, with a lack of stereospecificity in several of the synthetic steps, producing forms which are difficult to separate.

Chemical synthetic procedures are known for converting daunomycin to doxorubicin; however they require the use of halogens in the synthetic process.

It would be desirable to have an efficient, cost-effective method for producing doxorubicin that does not require the use of halogens in the synthetic process.

SUMMARY OF THE INVENTION

The present invention provides novel methods for producing doxorubicin using daunomycin as a substrate. One method employs a genetically engineered host microorganism which is transformed with a vector, preferably a plasmid, which contains the doxA gene. Preferably, the doxA gene, also referred to herein as "doxA", is cloned into a plasmid which is then introduced into the host microorganism, preferably a bacterial host, more preferably Streptomyces, to provide a transformed host microorganism. The doxA gene, when present on a plasmid, confers on the transformed host the ability to convert daunomycin and 13-dihydrodaunomycin, to doxorubicin. The doxA gene encodes a cytochrome P450-type enzyme which catalyzes the hydroxylation of daunomycin and 13-dihydrodaunomycin at C-14 to form doxorubicin; such enzyme is designated "daunomycin C-14 hydroxylase". Thus, the expression of doxA in the transformed host using a plasmid which contains doxA enables the transformed host to convert daunomycin to doxorubicin. The doxorubicin is then extracted from host microorganism cultures.

Another method for producing doxorubicin involves incubating the daunomycin C-14 hydroxylase with daunomycin, then extracting the doxorubicin from the solution.

Another method involves adding daunomycin to cultures of Streptomyces sp. strain C5 and extracting doxorubicin from the culture fluid and the host cells.

The invention also relates to daunomycin C-14 hydroxylase, novel plasmids, novel polylinkers and novel transformed host microorganisms employed in such method for producing doxorubicin. The invention also relates to methods for producing anthracyclines, such as 13-deoxycarminomycin and 13-deoxydaunomycin, 13-dihydrocarminomycin and 13-dihydrodaunomycin, carmninomycin and daunomycin.

BRIEF DESCRIPTION OF FIGURES

FIG. 3A and 3B is a nucleotide sequence of the 3196 base pair KpnI- SstI DNA fragment from Streptomyces sp. strain C5 containing the doxA gene. The deduced amino acid sequence of the daunomycin C-14 hydroxylase is given below the nucleotide sequence. Potential ribosome binding sites, designated "rbs" are identified, as are significant restriction endonuclease sites. The sequences and deduced products of the 3' end of orfl, all of orfA, and the 5' end of dauI are also shown;

FIG. 6 shows the sequence of snpR, doxA, and the intervening sequences within plasmid pANT195;

FIG. 7 shows plasmid maps of pANT192 and pANT193;

FIG. 9 shows the N-terminal, modified region of the doxA fusion protein;

FIG. 10 shows plasmid maps of pANT198 and pANT199; and

FIG. 11 shows sequence of the doxA gene and upstream melC1 promoter regeion in pANT196.

DETAILED DESCRIPTION OF INVENTION

A novel method for producing doxorubicin from daunomycin has been developed which employs genetically engineered host microorganisms that contain and express the gene doxA. Preferably, doxA is cloned into a plasmid which is then inserted into a host microorganism, preferably a bacterial host, more preferably Streptomyces, most preferably *Streptomyces lividans* to provide a transformed host. The doxA gene encodes daunomycin C-14 hydroxylase which catalyzes the hydroxylation of daunomycin and 13-dihydrodaunomycin at C-14 to form doxorubicin. Thus, expression of doxA in the transformed host using a plasmid which contains the doxA gene enables the transformed host to convert daunomycin to doxorubicin.

Daunomycin is also known as daunorubicin; doxorubicin is also known as 14-hydroxydaunomycin and adriamycin. The structure of daunomycin is shown below:

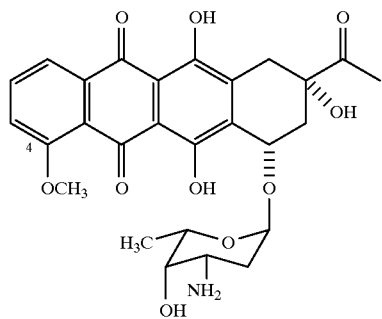

The structure of doxorubicin is shown below:

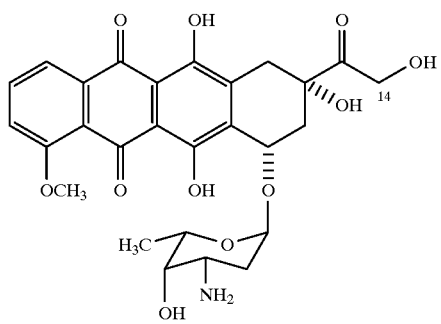

Cloning and Analysis of the DoxA Gene

Streptomyces sp. strain C5 synthesizes several compounds in fermentations, that is such compounds are produced from common metabolic intermediates and without the addition of precursor anthracycline molecules to the culture media. Streptomyces sp. strain C5 produces the following anthracyclines: e-rhodomycinone; daunomycin; 13-dihydrodaunomycin; baumycin A1; and baumycin A2. Nevertheless, a gene, the doxA gene, was discovered in the genome of Streptomyces sp. strain C5 which, when expressed, converts daunomycin, particularly exogenous daunomycin, to doxorubicin. Preferably, the conversion of daunomycin to doxorubicin is accomplished by cloning the doxA gene along with a promoter into a plasmid which is then introduced into a host microorganism.

It has also been discovered that Streptomyces sp. strain C5 can convert small amounts, less than 10%, daunomycin to doxorubicin in the absence of plasmid containing the doxA gene.

Preferably, the doxA gene is cloned from Streptomyces, preferably Streptomyces sp. strain C5. Alternatively, the doxA gene is synthesized using conventional oligonucleotide synthesis techniques and equipment.

Figure 1:
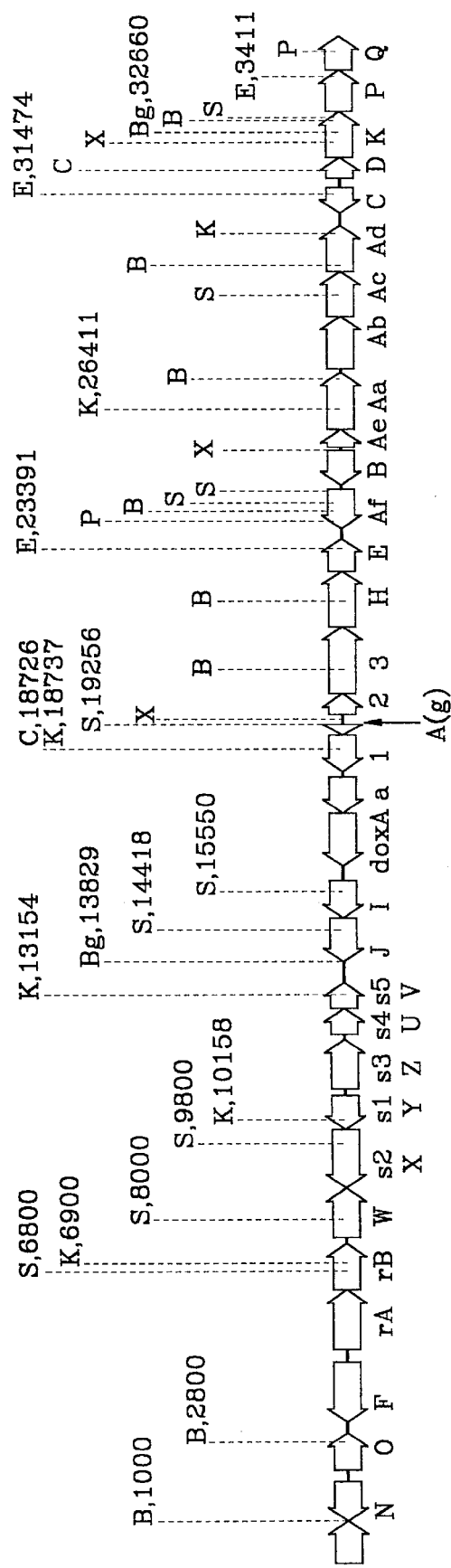
FIG. 1 is a restriction map of the Streptomyces sp. strain C5 daunomycin biosynthesis gene cluster which shows the position of doxA within the cluster. Abbreviations for restriction endonuclease sites are as follows: "B" represents BamHI; "Bg" represents BglII; "C" represents ClaI; "E" represents EcoRI; "K" represents KpnI; "P" represents PstI; "S" represents SstI; and "X" represents XhoI.
Figure 2:
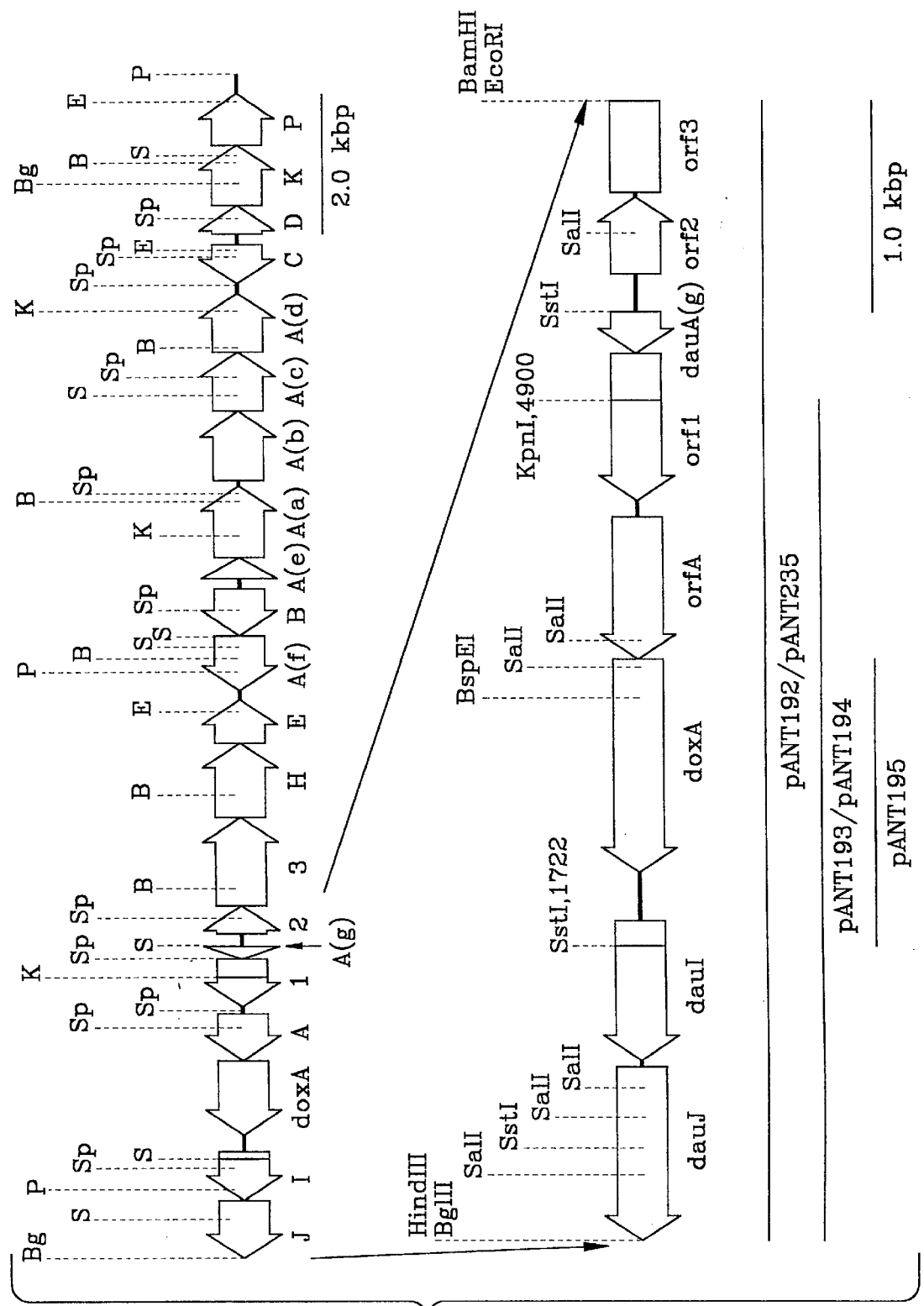
FIG. 2 is a detailed restriction map of part of the daunomycin biosynthesis gene cluster from Streptomyces sp. strain C5. Abbreviations for restriction endonuclease sites are as follows: "B" represents BamHI; "Bg" represents BglII; "E" represents EcoRI; "K" represents KpnI; "P" represents PstI; "S" represents SstI; "Sp" represents SphI.

The doxA gene is located in the daunomycin biosynthesis gene cluster between the daunomycin polyketide biosynthesis genes and dauI, a putative transcriptional activator as shown in FIG. 1. The location of doxA within the Streptomyces sp. strain C5 daunomycin biosynthesis gene cluster is shown in FIG. 2.

The approximately 8 kbp region between dauI, a gene encoding an activator regulatory protein for daunomycin biosynthesis, and the daunomycin polyketide synthase biosynthesis genes was sequenced in its entirety.

Plasmids containing inserts to be sequenced were isolated from recombinant *E. coli* JM83, available from Dr. Mary Berlyn, *E. coli* Genetic Stock Center, Yale University, P.O. Box 6666, New Haven, Conn. 06511-7444 by the methods disclosed in Carter, M. J., and I. D. Milton, (1993), "An Inexpensive and Simple Method for DNA Purification on Silica Particles," *Nucleic Acid Res.* Volume 21, p. 1044. The doxA DNA was sequenced in both directions, that is, both strands were sequenced using Sequenase enzyme, Version 2.0 from the United States Biochemical Corp., Cleveland, Ohio, according to the manufacturer's instructions, and as described in Ye, et. al., 1994, "Isolation and Sequence Analysis of Polyketide Synthase Genes from the Daunomycin-producing Streptomyces sp. strain C5 " *J Bacteriol.* 176:6270–6280. Doubled-stranded DNA templates were employed. The terminated chains were labeled with 3000 Ci/mmol (a- $^{32}$P)dCTP from Dupont -New England Nuclear, Boston, Mass. The terminated labeled chains were separated on a 6% weight-to-volume polyacrylamide gel containing 10% (volume-to-volume) formamide and visualized by autoradiography. Sequencing reactions were carried out using 7-deaza-dGTP nucleotide mixes to reduce compressions. Forward (-40) and reverse universal pUC/m13 17-mer oligonucleotide primers from U.S. Biochemical Corp. were used to obtain the initial sequences in the inserts. Specific primers, 15-mer oligonucleotides, were generated based on sequencing results for extension of the sequences within the inserts.

DNA sequence data were analyzed using Clone Manager from Stateline, Pa., and the Sequence Analysis Software Package of the Genetics Computer Group from Madison, Wis.

The nucleotide sequence between dauI and the ketoreductase just downstream of dauA-orfG is shown in FIG. 3. Two complete open reading frames, orfA and doxA, were found within this sequence; OrfA encodes a protein of $M_r 28,808$, and 275 amino acid residues, and doxA encodes a protein of $M_r 46,096$ and 422 amino acid residues.

Plasmids

The doxA gene is inserted into a vector, preferably a plasmid. Optionally, the plasmid contains genes from the daunomycin synthesis cluster in addition to doxA. However, preferred plasmids lack dauA(g) and more preferred plasmids lack dauA(g), orfI and orfA.

The preferred plasmids contain not only the translated portion of doxA but a promoter. Suitable promoters include, Streptomyces promoters for example, melC1-P, ermE-P, wild type, and snpA-P. The snpA-P promoter is the most preferred. Preferably, the promoter is a protein activated promoter, and most preferably, an SnpR-activated promoter. Less preferred plasmids, such as pANT196, contain a melC1 promoter from pIJ702 for expression of doxA. Also less preferred are plasmids which lack a known promoter, such as pANT194.

Figure 5:
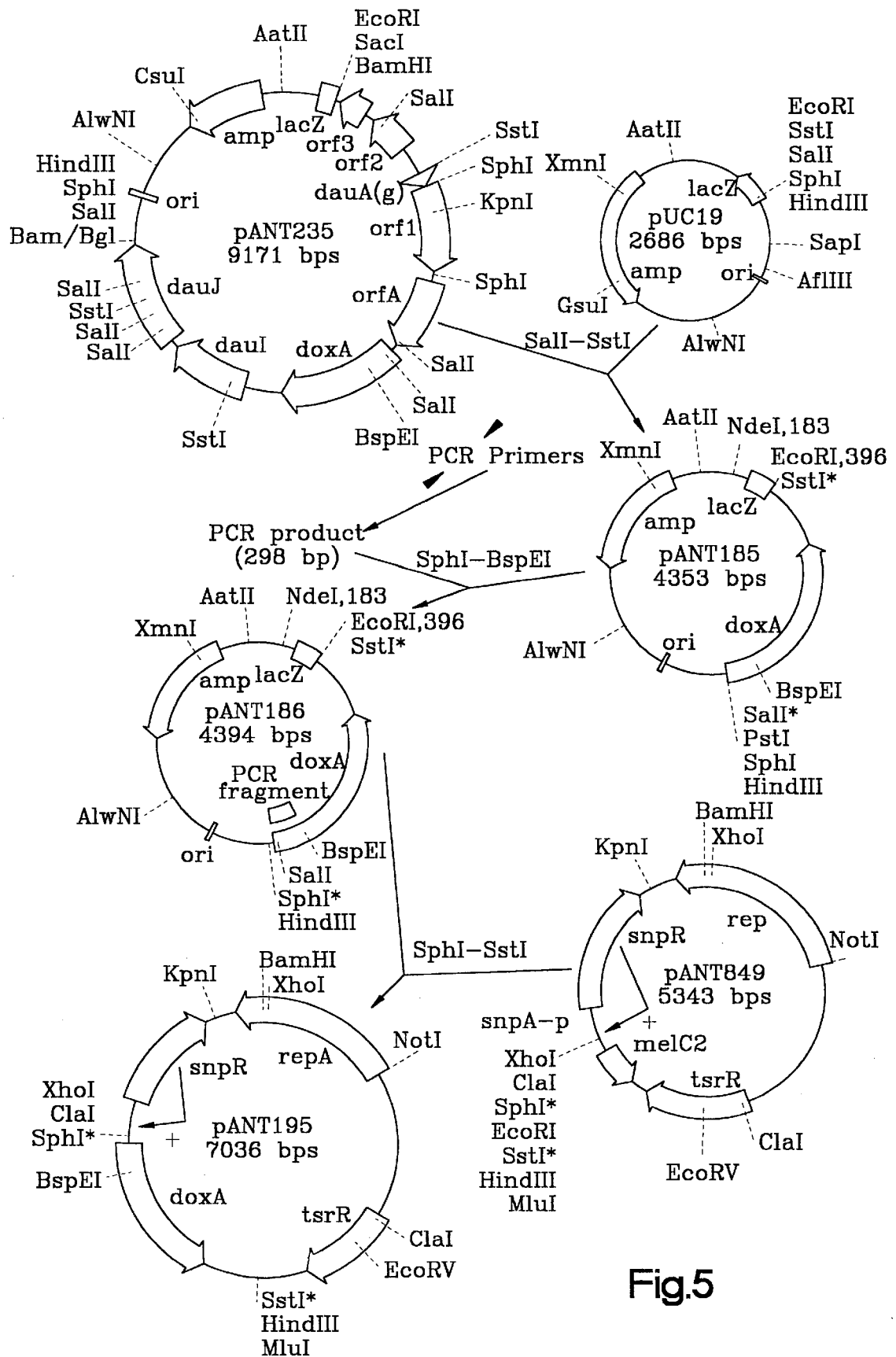
FIG. 5 shows the plasmid maps of pANT195 and plasmids pANT849, pANT186, pANT185, pANT235 and pUC19 all of which were used to construct pANT195.

The most preferred plasmid which contains doxA is designated "pANT195" which is shown in FIG. 5. Host microorganisms, when transformed with plasmid pANT195, convert 100% daunomycin to doxorubicin. Other plasmids which contain doxA are suitable, including, for example pANT192, pANT193, pANT194 and pANT196. Host microorganisms, when transformed with plasmid pANT192, typically convert about 25% daunomycin to doxorubicin at a concentration of 2 mg/ml. Host microorganisms when transformed with pANT193 convert about 80% daunomycin to doxorubicin and about 20% daunomycin to 13-dihydrodaunomycin, at a daunomycin concentration of 2 mg/ml.

Construction of the Plasmids

Digestion of and ligation of DNA was performed using conventional techniques described by Maniatis et al. (1982) in "Molecular Cloning: A Laboratory Manual," Cold Spring Harbor Laboratory, New York.

Construction of pANT195

Plasmid pANT195, shown in FIG. 5, has about 7.04 kbp of DNA. Plasmid pANT195 was constructed by inserting the 1.72 kbp SphI-SacI fragment insert containing intact doxA from plasmid pANT186 into pANT849.

First, plasmid pANT186 was constructed by constructing pANT235. Plasmid pANT235 is described in Ye et. al. 1994 "Isolation and Sequence Analysis of Polyketide Synthase Genes from the Daunomycin-Producing Streptomyces sp. Strain C5 " *J Bacteriol*. Vol. 176, pp. 6270–6280. Plasmid pANT235 is a 9.2 kbp plasmid which contains a 6.48 kbp BamHI-BglII DNA fragment from the Streptomyces sp. strain C5 daunomycin biosynthesis gene cluster. The doxA gene lies within the insert of pANT235 which is derived from the daunomycin biosynthesis gene cluster. The BamHI-BglII DNA fragment had been cloned into the BamHI site of pUC19 to generate pANT235. Plasmid pUC19 is available from Gibco BRL, Gaithersburg Md.

Next, pANT235 was digested with SalI and SstI and the digestion products were purified on an agarose gel. The 1.67 kbp SalI-SstI fragment containing the 3_end of the doxA gene and the 5_end of daul was extracted from the agarose gel and ligated into pUC19 with T4 DNA ligase, from Gibco BRL, Gaithersburg Md., to generate pANT185, as shown in FIG. 5.

Next, pANT235 was used as the template for the polymerase chain reaction amplification of the 5_-end of the doxA gene containing an upstream ribosome binding site and SphI restriction site for the 5' end and BspEI restriction site for the 3' end.

The forward primer used in the polymerase chain reaction amplification of the doxA gene had the following nucleotide sequence: 5_-GACATGCATGCGGAGGGGTGCCTC-3_ SEQ ID NO:1 The forward primer which is used for the 5_-end, contains an SphI site with five extra nucleotides on the end and the extra ribosome binding site "GGAGG". The reverse primer had the following nucleotide sequence: 5_-GACGCAGCTCCGGAACGGGG-3_SEQ ID NO:2 The reverse primer which is used for the 3_-end, has a BspEI site plus eight extra nucleotides.

The polymerase chain reaction amplification was carried out for 25 cycles using Deep Vent Polymerase from New England Biolabs, Beverly, Mass. The solution for PCR included: 2.0 ml dimethylsulfoxide; 14.5 ml double distilled water; 1.25 mM dNTPs, 16.0 ml of a total stock containing DATP, dCTP, dTTP, dGTP; 5.0 ml 10×Deep Vent Buffer, from New England Biolabs; 5 ml forward primer; 5 ml reverse primer; 0.5 ml Deep Vent polymerase; 2.0 ml DNA template, 14.5 ml distilled water, and boiled for 10 minutes. PCR was carried out by incubating the reaction mixture at 94° C. in the absence of Deep Vent Polymerase for 5 minutes, following by 25 cycles of the following regimen: 94° C. for 30 seconds, 55° C. for 30 seconds, 72° C. for 30 seconds. After 25 cycles were completed, the mixture was incubated at 72° C. for 7 minutes and then held at 4° C. until further use.

The products of PCR were separated on a 0.8% agarose gel, and a 298 base pair DNA fragment was eluted from the gel. The 298 base pair DNA fragment was then digested with SphI and BspEI to generate a 285 base pair fragment with "sticky" ends. pANT185 was digested with SphI and BspEI and the 285 base pair fragment ligated into pANT185 to generate pANT186 which was introduced into dam/dcm-minus *E. coli* strain ET12567. MacNeil, et. al. (1992) "Analysis of *Streptomyces avermitilis* Genes Required for Avermectin Biosynthesis Utilizing a Novel Integration Vector", *Gene*, vol. 111, pages 61–68. Plasmid pANT186 contains the complete doxA gene, upstream of which lay the newly constructed ribosome binding site having the nucleotide sequence GGAGG. The nucleotide sequence of the PCR-generated 5_end of the gene was confirmed by dideoxy sequencing.

Figure 4:
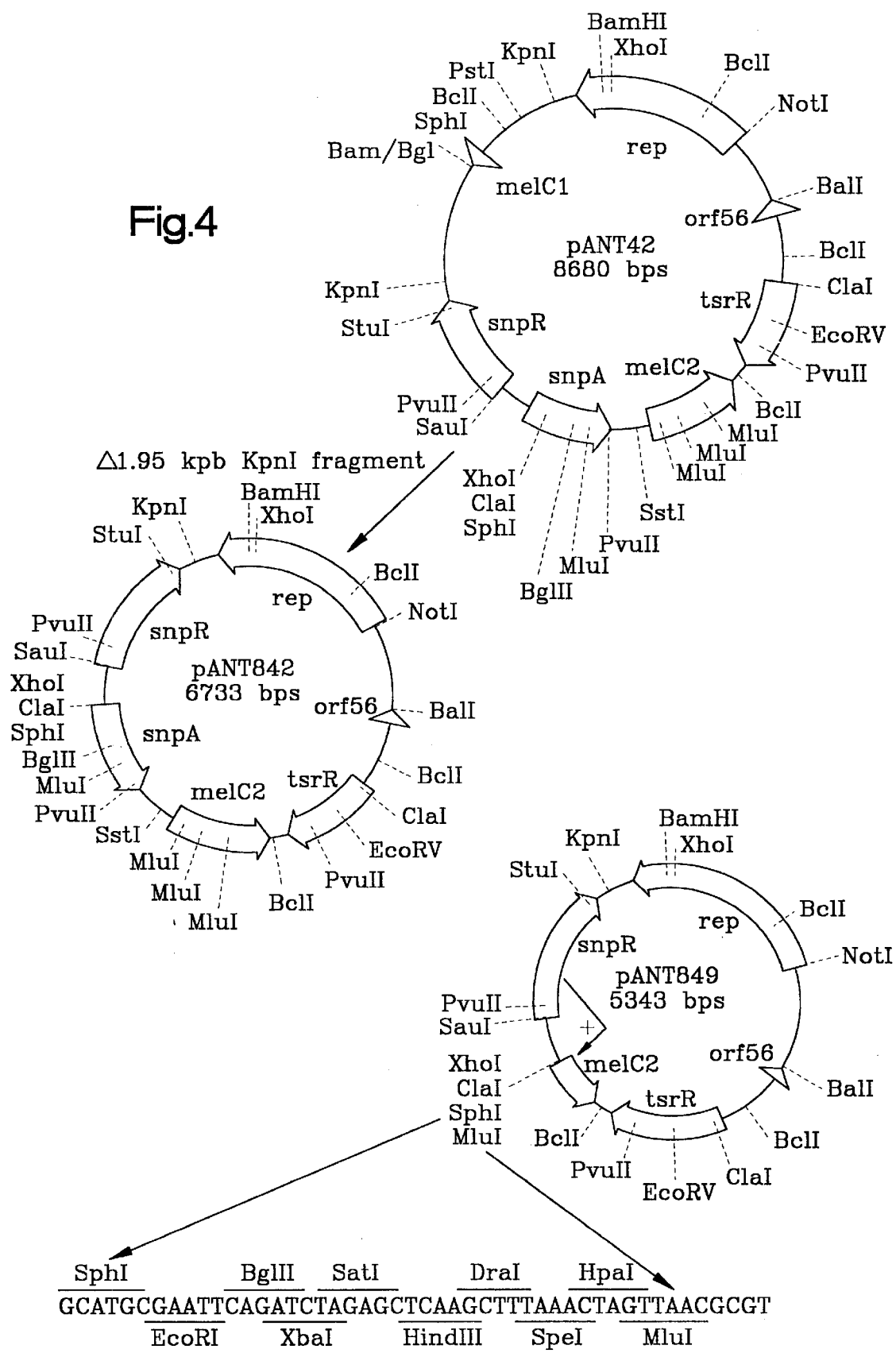
FIG. 4 shows the plasmid maps of plasmid pANT849 and the plasmids pANT42 and pANT842 which were used to construct pANT849.

Plasmid pANT849, shown in FIG. 4, was constructed by first constructing pANT842. Plasmid pANT42, described in Lampel, et. al., 1992 "Cloning and Sequencing of a Gene Encoding a Novel Extracellular Neutral Proteinase from Streptomyces sp. Strain C5 and Expression of the Gene in *Streptomyces lividans* 1326 "*J. Bacteriology* 174:2797–2808, was digested with KpnI and religated, removing a 1.95 kbp KpnI fragment to yield pANT842.

A novel polylinker sequence, having 48 nucleotides, was constructed according to conventional techniques using synthesized DNA oligonucleotides by Integrated DNA Technologies, Inc., Coralville, Iowa. The polylinker sequence has the following nucleotide sequence:

```
                                          SEQ ID NO:3
SphI BglIISacI DraI HpaI
GCATGCGAATTCAGATCTAGAGCTCAAGCTTTAAACTAGTTAACGCGT
    EcoRI XbaI HindIII SpeI MluI
```

Plasmid pANT842 was digested with SphI-MluI to remove a 1.42 kbp SphI-MluI fragment. The polylinker sequence was ligated into SphI-MluI-digested pANT842 to provide plasmid pANT849. Plasmid pANT849, shown in FIG. 4, has 5.34 kbp of DNA and lacks the snpA gene and most of melC2. Plasmid pANT849 does have the SnpR-activated snpA-promoter, which is located immediately upstream of the polylinker sequence as shown in FIG. 4. pANT849 is a high copy number plasmid and contains the thiostrepton resistance gene as the selectable marker.

Next, to construct pANT195, a clone of pANT186 which contains the modified doxA gene, was digested with SphI and SstI, and pANT849 was digested with SphI and SstI. The fragment from pANT186 containing the doxA gene was ligated into the polylinker sequence of pANT849 to make pANT195 as shown in FIG. 5.

The sequence of the region of pANT195 containing the snpR activator gene, the SnpR-activated snpA promoter, and the 5_-end-modified doxA gene is shown in FIG. 6, and SEQ ID NO:6.

Construction of pANT192

Plasmid pANT192 shown in FIG. 7 is an 11.84 kbp plasmid which contains DNA encoding the acyl carrier protein and its putative promoter, a ketoreductase (orf1), orf2, a partial orf3, orfA, doxA, dauI, and most of dauJ. Plasmid pANT192 was constructed by removing the 6.52 kbp HindIII-EcoRI fragment from pANT235 which includes the entire BglII-BamHI fragment, by digesting pANT235 with HindIII and EcoRI. Next pANT849 was digested with HindIII and EcoRI and the 6.52 kbp HindIII-EcoRI fragment from pANT235 was ligated into pANT849.

Construction of pANT193

Plasmid pANT193, shown in FIG. 7, has 10.28 kbp of DNA and contains part of orf1, all of orfA, and doxA driven by the snpR-activated snpA-promoter. Plasmid pANT193 was constructed by digesting plasmid pANT235 with KpnI, and the 1582 base pair KpnI fragment removed. The plasmid was re-ligated to itself to form pANT235-k. Plasmid pANT235-k was digested with EcoRI and HindIII to remove the 4.95 kbp EcoRI-HindIII fragment. pANT849 was digested with EcoRI and HindIII and the 4.95 kbp EcoRI-HindIII fragment from pANT235-k was ligated into the digested pANT849.

Construction of pANT194

Figure 8:
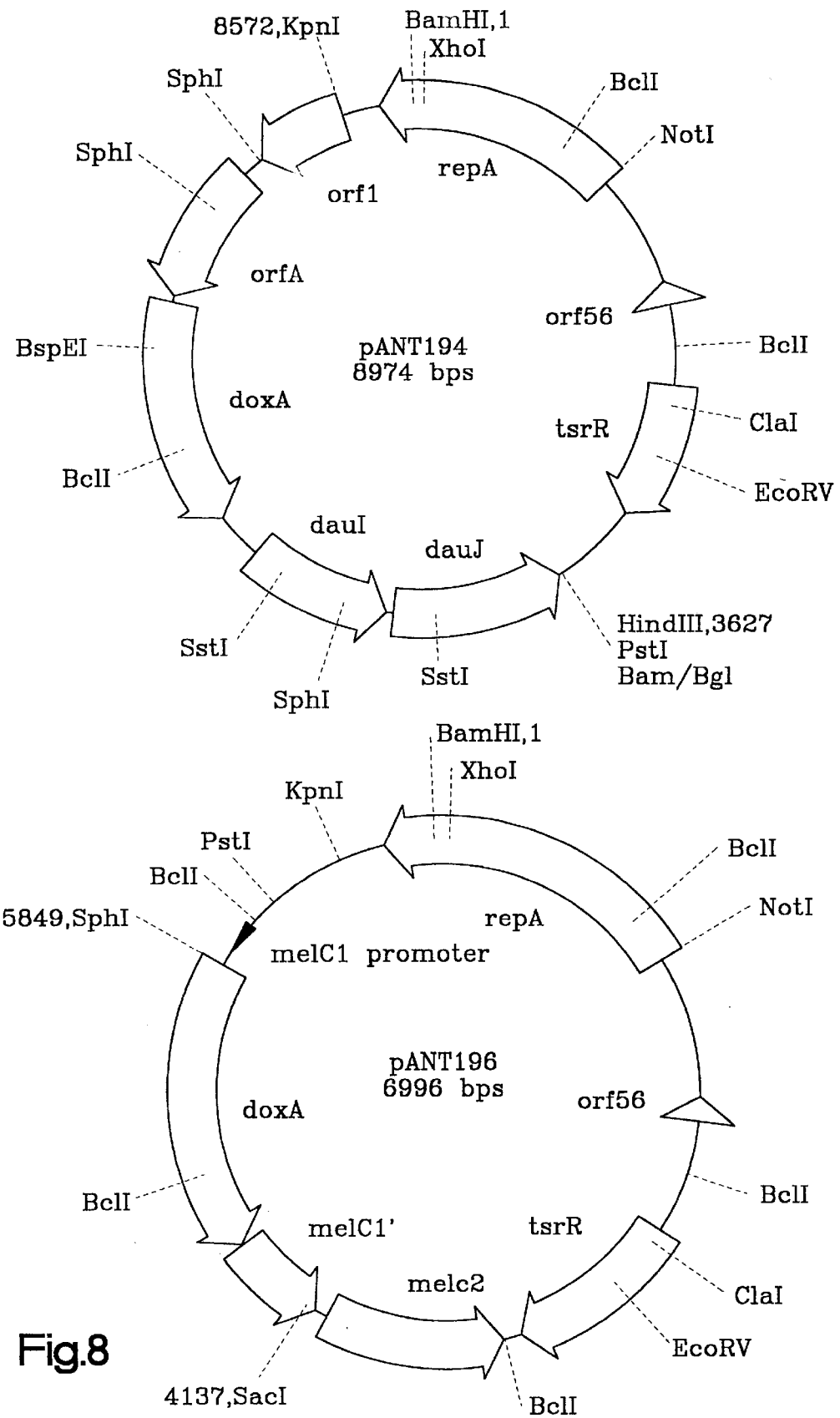
FIG. 8 shows plasmid maps of pANT194 and pANT196.

Plasmid pANT194, shown in FIG. 8, has 8.97 kbp of DNA and contains the part of orf1, all of orfA, dauI, dauJ and doxA but lacks any known promoter to drive the expression of doxA. Plasmid pANT194 was constructed by digesting pANT192 with KpnI to remove a 2.87 kbp KpnI fragment and then religating the plasmid to itself.

Construction of pANT196

Plasmid pANT196, shown in FIG. 8, has 7398 bp of DNA and possesses a promoter melC1 which drives the expression of the doxA gene. pANT186 was digested with SphI and SstI and a 1712 nucleotide SphI-SstI fragment from pANT186 containing doxA was isolated and ligated into SphI-SstI digested pIJ702. Plasmid pIJ702 is a 5.686 kbp plasmid which is described in Katz, E., et. al. (1983) "Cloning and Expression of the Tyrosinase Gene from *Streptomyces antibioticus* in *Streptomyces lividans*" J. Gen. Microbiol. volume 129, pages 2703–2714.

Construction of pANT198

Plasmid pANT186 was digested with SphI and then incubated with T4 DNA polymerase from Gibco BRL, according to the manufacturer's instructions to yield a blunt end. Plasmid pZero from Invitrogen, San Diego, Calif., was digested with EcoRI and then filled in 5' to 3' using Klenow fragment of DNA polymerase according to the manufacturer's instructions to provide a blunt end. Both fragments were purified according to the methods described in Carter, M. J. and I. D. Milton (1993), *Nucleic Acid Res.* volume 21, pages 1044. The fragments were precipitated in ethanol for one hour at −70° C. and then digested with SstI overnight. The plasmid and insert, each of which contains a single blunt end and an SstI end, were purified from an agarose gel and then ligated overnight with T4 DNA ligase at room temperature, to provide pANT198.

Construction of pANT199

Plasmid pANT198 was digested with EcoRI-HindIII, the EcoRI-HindIII fragment removed and ligated into pTrcHisC from Invitrogen to construct pANT199. In pANT199, the doxA gene is translationally fused with a leader sequence encoding six histidine residues, shown in SEQ ID NO:7 so that the fusion protein can be affinity purified on a nickel-agarose gel.

pANT849

Plasmid pANT849 in addition to being useful to construct pANT195 is also useful expression vector for other genes. To construct other such plasmids pANT849 is digested with at least one restriction endonuclease corresponding to the restriction sites in the polylinker, such as, for example, SphI, BglII, SacI, DraI, HpaI, EcoRI, XbaI, HindIII, SpeI, or MluI. The desired gene sequence to be inserted into the plasmid is provided with sticky ends corresponding to the sticky ends of the cut pANT849. The desired gene is then ligated into the plasmid to provide a new plasmid derived from pANT849.

Host Microorganisms

Suitable host microorganisms for the doxA plasmid possess electron donating, cytochrome P450 accessory proteins; suitable accessory proteins include for example, NADPH-:ferredoxin oxidoreductase and ferredoxin. The preferred host microorganisms are bacteria, more preferably *E. coli* or *Streptomyces* spp., most preferably *Streptomyces lividans* TK24 and *Streptomyces coelicolor* CH999. *Streptomyces coelicolor* CH999 is a mutant of *Streptomyces coelicolor* A3(2). *Streptomyces lividans* TK4 is available from Professor David A. Hopwood, Head, Department of Genetics, John Innes Centre, Norwich Research Park, Colney, Norwich NR4 7UH, United Kingdom. *Streptomyces coelicolor* CH999 is available from C. Khosla, Stanford University, Palo Alto, Calif. and Professor David A. Hopwood. *S. peucetius* is available from the American Type Culture Collection, 12301 Parklawn Drive, Rockville, Md., U.S.A. under the accession number 29050. Streptomyces sp. strain C5 was obtained from the Frederick Cancer Research Center, Frederick Md. Streptomyces sp. strain C5 is also available from the American Type Culture Collection, 12301 Parklawn Drive, Rockville, Md., U.S.A. under the Accession number ATCC Transformation of Host Microorganism The plasmids are introduced into the host microorganism using conventional techniques. For example, Streptomyces spp. are transformed using electroporation as described in Pigac and Schrempf (1995) "A Simple and Rapid Method of Transformation of *Streptomyces rimosus* R6 and Other Streptomycetes by Electroporation", *Appl. Environ. Microbiol.* vol. 61, pages 352–356, or by protoplast transformation. Streptomyces are preferably transformed using protoplast transformation as described in Hopwood, et. al. (1985), "Genetic Manipulation of Streptomyces: A Laboratory Manual", The John Innes Foundation, Norwich, UK. *E. coli* strains are transformed using conventional transformation procedures as described in Maniatis, et al. (1982) "Molecular Cloning: A Laboratory Manual" Cold Spring Harbor Laboratory, New York.

Plasmid pANT195 was introduced into *Streptomyces lividans* TK24 by protoplast transformation according to the procedures described in Hopwood et. al (1985), "Genetic Manipulation of Streptomyces: A Laboratory Manual", The John Innes Foundation, Norwich, UK. 500 ml of *Streptomyces lividans* TK24 protoplasts, were transformed with 10 ml of plasmid DNA, about 0.5 mg total, in 500 ml of T buffer for two minutes. The reaction was stopped with 500 ml of P buffer and the protoplasts were pelleted twice in a microcentrifuge for 7 seconds each spin. The pellets were then resuspended in 100 ml of P buffer and plated onto R2YE medium using a soft R2YE agar overlay with 50 mg/ml of thiostrepton added 24 hours later. The transformed microorganisms were tested for their ability to carry out daunomycin C-14 oxidation.

*S. peucetius* ATCC 29050, *Streptomyces coelicolor* CH999 and Streptomyces sp. strain C5 were transformed with plasmids pANT195 and pANT849 by protoplast transformation.

Daunomycin C-14 Hydroxylase

The daunomycin C-14 hydroxylase encoded by doxA is a cytochrome P450-type enzyme having a deduced Mr of 46,096. Daunomycin C-14 hydroxylase is a monooxygenase which inserts a single oxygen at carbon 14 on daunomycin. The daunomycin C-14 hydroxylase also appears to catalyze the two step oxidation at C-13 from methylene to hydroxyl to a keto functional group. Daunomycin C-14 hydroxylase also oxidizes 13-dihydrocarminomycin to carminomycin and 13-dihydrodaunomycin to doxorubicin.

The deduced amino acid sequence of daunomycin C-14 hydroxylase which is encoded by doxA of strain C5 is shown in FIG. 3 and SEQ ID NO:5.

Preparation of Daunomycin C-14 Hydroxylase

EXAMPLE A

The daunomycin C-14 hydroxylase was isolated and partially purified and subjected to spectrophotometric analysis. First, *S. lividans* TK24 strains containing plasmid pANT195 were grown in YEME medium containing 10 mg/ml thiostrepton for 48 hours at 30° C., harvested and washed by centrifugation and then broken in 100 mM, pH 7.5 sodium phosphate buffer using a French pressure cell at 15,000 lb/in$^2$. The cell debris and unbroken mycelia were pelleted by centrifugation at 10,000'g for 30 minutes at 4° C., after which the supernatant was analyzed by visible spectrometry. The cytochromes within the supernatant derived from the cultures were reduced by a few grains of sodium dithionite. The supernatant samples were bubbled with carbon monoxide for 1 minute prior to analysis. Spectra were obtained using a Beckman DU-64 single beam spectrophotometer and reduced-plus-CO minus reduced difference spectra were obtained by electronic subtraction.

Reduced-plus-CO minus reduced difference spectra of samples derived from cultures of *S. lividans* TK24 containing plasmid pANT195 revealed a peak at 450 nm, characteristic of cytochrome P450 enzymes. Such peak was not observed in samples derived from the control culture, which lack the doxA gene.

Proteins derived from both *S. lividans* TK24 containing plasmid pANT195 and the control culture *S. lividans* TK24 containing control plasmid pANT849, were visualized by sodium dodecylsulphate polyacrylamide gel electrophoresis. Samples derived from cultures containing plasmid pANT195 revealed a band with $M_r$ of about 42,000, close to the predicted size of daunomycin C-14 hydroxylase. This band was not present in samples derived from the control cultures.

EXAMPLE B

A 50 ml culture of *S. lividans* TK24 (pANT195) was grown for 48 hours in YEME medium plus 10 mg/ml thiostrepton as in Example 1. This culture was split into 2×25ml aliquots, each of which was used to inoculate a 1000 ml flask containing 225 ml of YEME medium plus 10 mg/ml thiostrepton, giving 2 fresh 250 ml cultures, which were grown as described in Example 1 for 48 hours. A 14-liter stirred tank fermentor containing 9.5 liters of YEME medium with 10 mg/ml of thiostrepton was inoculated with both 250 ml cultures, a total inoculum size of 500 ml, and the 10 L culture was incubated for 6 days under the following conditions: temperature, 28° C.; air flow, 1 volume air/volume culture/minute; agitation, 250 rpms. The culture was harvested by continuous centrifugation using a Heraeus 300 MD System, from Heraeus Sepatech, South Plainfield, N.J., at 15,000 rpm and a flow rate of 100 ml/min. The resultant pellet was frozen at −70° C. until further use. A small portion of the frozen pellet of *S. lividans* TK24 (pANT195) was thawed on ice in ice-cold 0.1 M sodium phosphate ($Na_2HPO_4$:$NaH_2PO_4$) buffer having a pH 7.5. The thawed suspension was passed twice through a 4° C. French Pressure cell at 15,000 pounds per square inch to break the cells. The broken cell suspension was centrifuged at 10,000×g for 30 minutes at 4° C. and the supernatant from this centrifugation step was kept on ice to provide an isolated partially purified daunomycin C-14 hydroxylase.

P450 Determination

A 100 ml aliquot of the daunomycin C-14 hydroxylase prepared according to Example B, was added to 900 ml of 0.1M sodium phosphate buffer having a pH of 7.5, in a cuvette and approximately 1 mg of sodium dithionite was added to reduce the sample. This sample was used as the background for a spectrophotometric scan from 400 nm to 600 nm. Carbon monoxide was bubbled through this sample for one minute and the sample was scanned again from 400–600 nm. Electronic subtraction of the reduced plus carbon monoxide minus reduced sample revealed a sharp peak at 450 nm, indicative of the active cytochrome P450 enzyme. This assay was used before, during and after Examples 19 to 26 to ensure that the daunomycin C-14 hydroxylase was active and stable. In all cases, the cytochrome P450 activity appeared to be 100% of the original.

Method C

The Fusion Protein

Plasmid pANT199 was introduced by transformation into *E. coli* strain TOP10 from Invitrogen. Transformants were selected using ampicillin and grown in 3.0 ml cultures of SOB medium overnight at 37° C. The recipe for the SOB medium was provided by Invitrogen. Fifty mL of this culture was used to inoculate 3.0 ml of fresh SOB medium. The new culture was grown at 37° C. for 2 hours to an optical density of 0.6 and then induced with IPTG at 1.0 mM final concentration for 5 hours. The culture was then harvested by centrifugation in a microcentrifuge and the pellet was frozen overnight at −20° C. The next day the pellet was boiled in SDS-PAGE sample buffer described in Laemmli, U.K. (1970) "Cleavage of Structural Proteins during the assembly of the head of Bacteriophage T4" Nature volume 227, pages 680–685, and run on a 10% (w/v) SDS-PAGE gel. A protein with $M_r$ of about 52,000 was observed that was insert-specific, the approximate size expected for the fusion protein based on amino acid sequence.

The fusion protein is then bound to a nickel-agarose column from Invitrogen, Inc., San Diego, Calif., and washed with 50 mM sodium phosphate buffer at pH 8.0 containing also 300 mM NaCl and 20 mM imidazole. The protein is then eluted using the same buffer but containing with 250 mM imidazole buffer at pH of 8, to provide a pure fusion protein with a modified N-terminus as shown in FIG. 9 and SEQ ID NO:8. The leader sequence is then cleaved from the fusion protein using enterokinase available from Biozyme Lab. Int'l Ltd. San Diego Calif., according to the manufacturer's directions, to provide pure N-terminal-modified daunomycin C14 hydroxylase as shown in SEQ ID NO:9.

Methods of Converting Daunomycin to Doxorubicin

A host microorganism transformed with a plasmid containing the doxA gene is grown preferably in liquid culture, and daunomycin is added to the culture broth. Preferably, the daunomycin is added at a concentration of from about 2 mg/L to 22.2 mg/L, more preferably about 2 to 10 mg/L. Preferably, the daunomycin concentration is below about 10 mg/L. Where the concentration is above about 10 mg/L, the daunomycin tends to kill the host microorganisms although doxorubicin is still produced. The culture of transformed host microorganism is then incubated with the daunomycin; the longer the incubation the greater the amount of daunomycin is converted to doxorubicin. Preferably, the culture is incubated at least 6 hours, more preferably, at least 24 hours with the daunomycin.

A 48 hour culture has sufficient biomass to convert 2 mg/L daunomycin to doxorubicin within 24 hours.

Next, the doxorubicin is extracted preferably from both the transformed microorganisms and the culture fluid, using conventional techniques. A suitable technique involves extracting the transformed microorganisms and the culture fluid, preadjusted to a pH of about 8.5, with a mixture of chloroform and methanol and separating and drying the organic phase to provide a culture extract. The culture extract is resuspended in methanol and the components of the culture extract are separated, preferably by chromatography, to provide doxorubicin.

Media Composition

GPS production medium contains: glucose, 22.5 g/L; Proflo from Traders, Memphis, Tenn., 10 g/L; NaCl, 3 g/L; CaCO$_3$, 3 g/L, and 10 ml/L trace salts according to Dekleva, M. L. et. al. (1985), "Nutrient Effects on Anthracycline Production by *Streptomyces peucetius* in a Defined Medium", *Canad. J. Microbiol.* vol. 31, pages 287–294.

APM seed medium contains the following: yeast extract, 8 g/L; malt extract, 20 g/L; NaCl, 2 g/L 3-(N-morpholino) propanesulfonic acid buffer, 15 g/L; antifoam B from Sigma Chemical Co., St. Louis, Mo., 4 ml/L; 10% weight to volume MgSO$_4$, 1 ml/L; 1% weight to volume FeSO$_4$, 1 ml/L; 10% weight to volume ZnSO$_4$, 0.1 ml/L; 50% weight to volume glucose, 120 ml/L, added after autoclaving; tap water to 1.0 L as described in Guilfoile and Hutchinson, (1991), "A Bacterial Analog of the mdr Gene of Mammalian Tumor Cells is present in *Streptomyces peucetius*, the Producer of Daunorubicin and Doxorubicin", *Proc. Nat'l. Acad. Sci. USA* volume 88, pages 8553–8557.

The YEME medium contained 3 g/L yeast extract available from U.S. Biohemical Corp. Cleveland, Ohio; 5 g/L bacto-peptone from Difco Detroit, Mich.; 3 g/L Difco malt extract; 10 g/L glucose; 200 g/L sucrose; and 2 ml/L of an autoclave-sterilized solution of 2.5 M MgCl$_2$×6H$_2$O. The pH was adjusted to 7.2 and the solution was autoclaved at 121° C. for 20 minutes at 15 psi, to provide the YEME medium.

The nitrate-defined-plus-yeast extract medium, also referred to herein as "NDYE medium", contains the following: yeast extract, 5.0 g/L; N-(2-hydroxyethyl)piperazine-N_-(2-ethanesulfonic acid) buffer 4.8 g/L; 0.06 g/L anhydrous MgSO$_4$; 0.24 g/L K$_2$HPO$_4$×3H$_2$O; 4.28 g/L NaNO$_3$; 1.0 ml/L 20×trace elements; 45% (w/v) glucose solution, 50 ml/L; pH 7.3. The 20×trace elements solution contains the following elements in double distilled water: ZnCl$_2$, 800 mg/L; FeCl$_3$×6H$_2$O, 4000 mg/L; CuCl$_2$×2H$_2$O, 40 mg/L; MnCl$_2$×4H$_2$O, 40 mg/L; Na$_2$B$_4$O$_3$×10H$_2$O, 40 mg/L; (NH$_4$)$_6$Mo$_7$O$_{24}$×4H$_2$O, 200 mg/L; NiCl, 100 mg/L as described by Dekleva et al. (1985) *Can. J. Microbiol* volume 31, pages 287–294. A few drops of Mazu DF60-P antifoam, obtained from Mazer Chemical Co., Gurney, Ill., were added to control foaming in cultures containing NDYE medium. Other antifoam agents, such as Sigma Antifoam B from Sigma Chemical Company, are also suitable.

EXAMPLES

The following examples are illustrative and not intended to be limiting.

Methods of Producing Doxorubicin Employing Host Microorganisms

Example 1

Cultures of *S. lividans* TK24 containing plasmid pANT195 and control cultures of *S. lividans* TK24 containing plasmid pANT849 were grown on R2YE agar medium containing 10 mg/ml of thiostrepton in standard 100 mm×15 mm plastic petri dishes for 5 days at 30° C., at which time the entire cultures had sporulated. The spores from one entire petri plate were used to inoculate 50 ml of modified YEME medium in 250 ml erlenmeyer flasks. Then 10 mg/ml thiostrepton in DMSO were added to the medium. The thiostrepton was added as selective pressure to maintain the plasmids. The cultures were grown for 48 hours at 30° C. with rotary shaking at 250 rpm, one inch throw on the shaker. After 48 hours, a 1.5 ml sample was removed for plasmid analysis to ensure the presence and size of the insert DNA containing the doxA gene using a "mini-prep" procedure according to Carter, M. J., and I. D. Milton, (1993), "An Inexpensive and Simple Method for DNA Purification on Silica Particles," *Nucleic Acid Res.*, Vol. 21, page 1044. Restriction endonuclease digestion with BspEI and agarose gel electrophoresis generated 1.7 kbp, 2.2 kbp, and 3.14 kbp fragments which indicated an intact plasmid and insert. Then a 10 mL solution containing 100 mg of filter sterilized daunomycin-HCl in distilled water was added to the cultures for a final concentration of 2.0 mg of daunomycin per ml of culture broth. Incubation was continued for 72 hours.

After a total of 120 hours, that is, 48 hours growth and another 72 hours of continued growth in presence of the daunomycin, the pH of the culture was 7.6. The remaining culture broth, a volume of 48.5 ml, was brought to pH 8.5 with the dropwise addition of 5 N NaOH. Then the whole culture broth, including culture fluid and cells, was extracted once with a 2×volume of chloroform:methanol at a ratio of 9:1. The organic phase was separated from the aqueous phase by centrifugation at about 10,000×g for 10 minutes and then the organic phase was removed by pipet. The organic phase was air dried in a chemical fume hood, then resuspended in 1 ml of 100% reagent grade methanol and spotted onto aluminum-backed, 0.25 mm silica gel thin layer chromatography plates from Whatman, Clifton, N.J. The components derived from the organic phase culture extract were separated using a solvent system of chloroform:methanol:acetic acid:water (80:20:16:6). The anthracyclines in the culture extracts were visualized on the plates by their normal pigmentation and by their fluorescence under ultraviolet irradiation at 365 nm. Table 1 shows the results.

The culture extracts of Example 1 and known standards also were separated and analyzed by high performance liquid chromatography using a $C_{18}$ mBondaPak reverse phase column from Waters Corp. Milford, Mass. The solutions of standards and culture extracts of Example 1 were filtered through 0.2 mm Nylon Acrodisc®13 filters from Gelman Sciences, Ann Arbor, Mich. and separated by HPLC using a mobile phase of methanol:water (65:35) brought to a pH of 2.5 with 85% phosphoric acid using a Waters 600E Multisolvent Delivery Pump and Controller and U6K 0-2.0 ml manual injector and detected on-line at 254 nm using a Waters 486 Tunable Absorbance Detector. The data were analyzed on-line and post-run using "Baseline 815" software and a 386 SX PC-compatible computer. The products extracted from the cultures were compared to standards run in parallel and by co-chromatography. These results are shown in Table 2.

TABLE 1

THIN LAYER CHROMATOGRAPHY OF DOXORUBICIN PRODUCED ACCORDING TO EXAMPLE 1 AS COMPARED TO KNOWN STANDARDS

| Sample | $R_f$ of Sample |
|---|---|
| Daunomycin Standard | 0.56 |
| Doxorubicin Standard | 0.36 |
| 13-Dihydrodaunomycin Standard | 0.39 |
| Doxorubicin from Cultures Containing Plasmid doxA (pANT195) | 0.36 |
| 13-Dihydrodaunomycin from Control Culture | 0.39 |

A few grains of each standard was reconstituted in 1 ml of methanol.

As indicated by the results in Table 1, the cultures transformed with plasmid pANT195 containing doxA which were incubated with daunomycin, produced doxorubicin. In contrast, the control cultures produced 13-dihydrodaunomycin. Co-chromatography confirmed these results.

TABLE 2

HIGH PERFORMANCE LIQUID CHROMATOGRAPHY OF DOXORUBICIN PRODUCED ACCORDING TO EXAMPLE 1 AS COMPARED TO KNOWN STANDARDS

| Sample | Retention time of sample[2] (minutes) |
|---|---|
| Daunomycin[1] Standard | 13.3 |
| Doxorubicin[1] Standard | 8.4 |
| 13-Dihydrodaunomycin Standard | 10.6 |
| Doxorubicin from doxA Transformants | 4.1; 7.2 (minor) |
| Control | 4.1; 10.6; 21.2 |

[1]Standards were reconstituted at 1.0 mg/ml in methanol.
[2]A methanol peak at 2.9 minutes was found in all samples.

The doxA transformants converted greater than 90% of the daunomycin to doxorubicin in 72 hours as evidenced by both TLC and HPLC analyses. The control cultures, which lack the doxA gene, converted daunomycin to 13-dihydrodaunomycin, but not to doxorubicin.

The culture extracts of Example 1 and the standards were hydrolyzed to their respective aglycones to verify the chemical structures. The acid hydrolysis product of the doxorubicin is adriamycinone, and the acid hydrolysis product of the 13-dihydrodaunomycin is 13-dihydrodaunomycinone. The acid hydrolysis product of the doxorubicin produced by Example 1 was adriamycinone. The acid hydrolysis product of the 13-dihydrodaunomycin produced by control cultures of Example 1 was 13-dihydrodaunomycinone.

Example 2

The procedure of Example 1 was repeated, with the following exceptions. The cultures were grown at 28° C. rather than 30° C., for 48 hours. After 48 hours of growth, 500 mg of daunomycin-HCl were added to the cultures for a final concentration of 10.0 mg/ml of daunomycin followed by further incubation for 36 hours, instead of 72 hours.

The culture broth then was extracted and the entire sample volume was spotted in a line onto a 250 mm layer thickness 20 cm×20 cm glass-backed TLC plate containing a fluorescent indicator (254 nm) from Aldrich, Milwaukee, Wis. The doxorubicin was separated from contaminants by chromatography for 2 hours using a mobile phase of chloroform:methanol:acetic acid:water (80:20:16:6), after which the silica gel containing the band having $R_f$, 0.3–0.4 was scraped from the plate. The silica gel was extracted three times with about 1.5 ml of methanol each time. The methanol extracts were combined, filtered through a 0.2 mm Nylon Acrodisc®13 filter, and air-dried. The dried product was resuspended in 500 mL of chloroform:methanol in a ratio of 9:1, back-extracted with an equal volume of water that had been previously made alkaline to pH 10.0 using $Na_2CO_3$, and the organic phase from this extraction procedure was removed and dried. The dried sample was resuspended in 500 mL of methanol, from which 50 mL were removed for HPLC and TLC analysis. HPLC analysis of this sample confirmed that doxA transformant cultures converted virtually all of the 500 mg of daunomycin to doxorubicin.

The remainder was redried and subjected for mass spectrometry analysis. MS spectra were recorded on a SCIEX API III+ triple quadruple mass spectrometer fitted with an atmospheric pressure chemical ionization source operating in a positive ion mode. MS spectra were acquired by scanning the first quadruple (Q1), the results are shown in Table 3.

TABLE 3

MS ANALYSIS ON THE DOXORUBICIN PRODUCED ACCORDING TO EXAMPLE 2

| Sample | Calculated MW | Average M + 1 |
|---|---|---|
| Daunomycin standard | 527.51 | 528.00 |
| Doxorubicin standard | 543.54 | 544.05 |
| 13-Dihydrodaunomycin standard | 529.50 | 530.01 |
| Doxorubicin from Transformants Containing doxA | — | 544.00 |

The results of the MS analysis, shown in Table 3, indicate that the doxorubicin from doxA transformed cultures has an M+1 of 544.00, essentially the same value as obtained with the doxorubicin standard. The M+1 value of the doxorubicin produced by the doxA transformed culture was not similar to the M+1 values obtained with either daunomycin standard or the 13-dihydrodaunomycin standard.

Example 3

A 50 ml culture of *Streptomyces lividans* TK24 (pANT195) culture was prepared as in Example 1. This culture was grown for 48 hours at 28° C. and then 25 ml were removed and used to inoculate 200 ml of YEME medium containing 10 mg/L of thiostrepton in a 1.0 L flask, having total, 225 ml of culture volume. After incubation for 48 hours at 28° C., 5.0 mg of daunomycin-HCl in 1000 ml of distilled water were added to the culture to give a final concentration of 22.2 mg/ml. A control culture of *S. lividans* TK24 containing plasmid pANT849 which lacks the doxA gene, was incubated in the presence of 100 mg of daunomycin-HCl. The cultures were incubated for 48 hours and then extracted as described in Example 1 and analyzed by HPLC and TLC. The doxorubicin which migrated in a broad band having an $R_f$ of 0.3–0.4 was separated from contaminants by chromatography and prepared for MS analysis as in Example 2. The results are shown in Table 4.

The doxA transformed culture converted essentially all of the 5 mg of daunomycin to doxorubicin. Notably, the doxA transformed culture was virtually dead at the end of 48 hours, whereas the cultures of Examples 1 and 2 which received 2 mg/ml of daunomycin were fully viable. Nevertheless, even though the culture was eventually killed by the daunomycin, the culture converted essentially all of the daunomycin to doxorubicin.

HPLC analysis showed that the doxA transformed cultures converted greater than 95% of the daunomycin to doxorubicin. The control culture converted essentially 100% of the daunomycin to 13-dihydrodaunomycin, and did not produce doxorubicin.

TABLE 4

MASS SPECTROPHOTOMETRY ANALYSIS ON THE DOXORUBICIN PRODUCED ACCORDING TO EXAMPLE 3

| Sample | Calculated MW | Average M + 1 |
|---|---|---|
| Doxorubicin Standard | 543.54 | 543.65 |
| 13-Dihydrodaunomycin Standard | 529.50 | 529.85 |
| Doxorubicin from Transfomants Containing doxA | — | 543.90 |
| 13-Dihydrodaunomycin from Control culture | — | 529.15 |

The results of the MS analysis, shown in Table 4, indicate that the doxorubicin produced by cultures containing plasmid pANT195, has an M+1 of 543.90, essentially the same as obtained with doxorubicin standard. An MS-MS analysis was run on the parent 543.9 peak and is shown in Table 5.

TABLE 5

MASS SPECTROPHOTOMETRY ANALYSIS OF DOXORUBICIN PRODUCED ACCORDING TO EXAMPLE 3

| Sample | M + 1 | Major fragmentation |
|---|---|---|
| Doxorubicin Standard | 543.65 489.90$^m$, 396.95, 378.70, | 360.45 345.95$^m$ 320.85 299.45 130.15 |
| Doxorubicin produced according to Example 3 | 543.90 396.80, 378.90, 361.00, | |
| 13-Dihydrodaunomycin Standard | 529.85 382.85, 365.30, 346.35, | 320.85, 129.35, 113.10 |
| Control culture extract | 529.15 497.20$^m$, 482.00$^m$, 382.80, | 364.60, 320.75, 305.75, 129.95 |

$^1$The product sample was significantly less concentrated than the standard sample, leading to recovery of only the most abundant fragmentation species.
$^m$-minor fragmentation species.

The MS-MS analysis on 543.90 peak from the doxorubicin produced in Example 3 shows daughter peaks which are essentially identical to the daughter peaks from the doxorubicin standard. Thus, the doxorubicin produced by the transformants containing doxA has the M+1 and MS/MS fragmentation patterns of standard doxorubicin. Similarly, the culture extract from the control culture had an M+1 and fragmentation pattern similar to that of standard 13-dihydrodaunomycin.

Example 4

Fifty ml cultures of *Streptomyces lividans* TK24 (pANT195) and *S. lividans* TK24(pANT849) as a control were inoculated and prepared as in Example 1 except that they were grown at 28° C. for 48 hours. At that time, 100 mg of daunomycin in 10 mL of distilled water was added to the cultures for a final concentration of 2 mg/ml. The cultures were further incubated for 24 hours. The cultures were then extracted as described in Example 1 and subjected to HPLC analysis.

The transformed culture containing the doxA gene converted greater than 95% of the daunomycin to doxorubicin within 24 hours. The control culture converted approximately 100% of the daunomycin to 13-dihydrodaunomycin.

Example 5

The procedure of Example 4 was repeated except that 100 mg of 13-dihydrodaunomycin, rather than daunomycin, were added to the cultures and the cultures were further incubated for 48 hours rather than 24 hours.

In 48 hours, the culture containing plasmid doxA (pANT195) converted 100% of the 13-dihydrodaunomycin to doxorubicin. The control culture did not convert the 13-dihydrodaunomycin.

Example 6

Fifty ml cultures of *Streptomyces lividans* TK24(pANT 196) and *S. lividans* TK24(pIJ702) as a control, were treated as in Example 4 except that the cultures were incubated with daunomycin for 72 hours.

The culture containing plasmid pANT196, which contains the doxA gene expressed from the melC1 promoter, converted 20% of the daunomycin to doxorubicin. Thus the melC1 promoter is less preferred than the snpA promoter. The control cultures converted 100% of the daunomycin to 13-dihydrodaunomycin.

Example 7

50 ml cultures of *Streptomyces lividans* TK24 (pANT192), having wild type and snpA promoters, *Streptomyces lividans* TK24(pANT193), having wild type and snpA promoters, *Streptomyces lividans* TK24(pANT194) which lacks the snpA-promoter and snpR activator gene, and *S. lividans* TK24(pANT849) as a control, were prepared and analyzed prepared as in Example 4, except that the cultures were incubated in the presence of the daunomycin for 48 hours. The results are presented in Table 6.

TABLE 6

COMPARISON OF DIFFERENT PLASMIDS ON PERCENT CONVERSION OF DAUNOMYCIN TO DOXORUBICIN

| Plasmid | Products |
| --- | --- |
| pANT192 | 75% 13-dihydrodaunomycin/25% |
| pANT193 | 80% doxorubicin/20% 13- |
| pANT194 | 90% 13-dihydrodaunomycin/ |
|  | 10% doxorubicin |
| pANT195 | 100% doxorubicin |
| pANT849 (control) | 100% 13-DHD |

As shown in Table 6, the culture containing pANT192, which contains doxA, converted 25% of daunomycin to doxorubicin and 75% of daunomycin to the 13-dihydrodaunomycin. The culture containing plasmid pANT193, which contains doxA, converted 80% of daunomycin to doxorubicin and 20% of daunomycin to the 13-dihydrodaunomycin. The culture containing plasmid pANT194, which contains doxA but lacks the snpA-promoter and snpR activator, converted 10% of daunomycin to doxorubicin and 90% of daunomycin to the 13-dihydrodaunomycin. The control culture converted the daunomycin to 13-dihydrodaunomycin, but not doxorubicin.

Example 8

Fifty ml cultures of *Streptomyces lividans* TK24 (pANT195) and *S. lividans* TK24(pANT849) as a control, were prepared as in Example 4, except that the pH of the YEME medium was adjusted before inoculation using NaOH or HCl to provide an initial culture pH as shown in Table 7. The cultures were further incubated for 48 hours, rather than 24 hours. The results are shown in Table 7.

TABLE 7

EFFECT OF CULTURE PH ON DOXORUBICIN PRODUCTION

| Initial pH | Final pH | Percent Daunomycin bioconverted to Doxorubicin |
| --- | --- | --- |
| 6.0 | 7.0 | 50% |
| 6.5 | 7.6 | 90% |
| 7.0 | 7.9 | 100% |
| 7.5 | 7.0 | 100% |
| 8.0 | — | No growth or bioconversion |

The % conversion is approximate.

The culture containing plasmid pANT195 which contains doxA, and which was initially at pH of 7.0 or 7.5, converted 100% of the daunomycin to doxorubicin. The cultures containing plasmid doxA which were initially at pH 6.0 converted 50% of the daunomycin to doxorubicin. The cultures containing plasmid doxA which were initially at pH 6.5 converted 90% of the daunomycin to doxorubicn. Accordingly it is preferred that the transformed host cultures be grown at an initial pH of higher than 6.5.

Example 9

The procedure of Example 4 was repeated except that cultures were grown at either 22° C., 28° C., or 37° C. and incubated with the daunomycin for 48 hours at such temperatures.

All three of the cultures containing plasmid doxA converted 100% of the daunomycin to doxorubicin.

Example 10

A 50 ml culture of *Streptomyces lividans* TK24 (pANT195), inoculated and prepared as in Example 1, was grown at 28° C. for 48 hours. At that time, the cultures were harvested by centrifugation at 10,000'g in a high speed centrifuge, washed once with 100 mM 3-(N-morpholino) propanesulfonic acid buffer at pH 7.2. The cells from the cultures were reconstituted in 5.0 ml of the 100 mM 3-(N-morpholino)propanesulfonic acid buffer to give a final volume of 6.0 ml which included the volume of the packed cell mass, resulting in an approximately 8-fold concentration of the recombinant mycelia in buffer. Then 100 mg of daunomycin were added in 10 mL of distilled water for a final concentration of 16.7 mg/ml of daunomycin. A concentration of 16.7 mg/ml of daunomycin is toxic to the host. The culture was further incubated for 7.0 hours, after which it was extracted as described in Example 1 and subjected to HPLC analysis.

In 7 hours, the concentrated cultures containing the plasmid with a doxA insert converted about 25% of the daunomycin to doxorubicin.

Example 11

Five ml each of APM seed medium containing 10 mg/ml of thiostrepton were inoculated by loop from R2YE agar plates, containing 50 mg/ml thiostrepton of *S. peucetius* 29050(pANT195) and *S. peucetius* 29050(pANT849). Each culture was grown at 28° C. for 48 hours. Fifty ml each of GPS "production" medium containing 10 mg/ml of thiostrepton were inoculated with 2.5 mls of seed culture grown in APM seed medium. The cultures were grown at 28° C. for 48 hours as in Example 1. Then 100 mg of daunomycin in 10 mL of distilled water for a final concentration of 2 mg/ml of daunomycin was added to the cultures. The cultures were further incubated for 48 hours, then extracted as described in Example 1.

After 48 hours, the culture containing plasmid pANT195, which contains the doxA gene, converted about one-half of the daunomycin to doxorubicin. The control cultures did not convert daunomycin to doxorubicin.

Example 12

Fifty ml cultures of *Streptomyces coelicolor* CH999 (pANT195), and *Streptomyces coelicolor* CH999 (pANT849) as a control, were used in the procedure of Example 4 except that the cultures were incubated with the daunomycin for 48 hours.

Again the cultures containing pANT195 converted 100% of the daunomycin to doxorubicin, while the control converted 80% of the daunomycin to 13-dihydrodaunomycin. In the control cultures 20% of the daunomycin was not converted.

Example 13

The procedure of Example 12 was repeated, except that after the daunomycin addition, the cultures were only incubated for 1, 2, or 4 hours.

After 1 hour, 0.7% of the daunomycin was converted to doxorubicin by the cultures which contained pANT195. After 2 hours, 1.0% of the daunomycin was converted and by 4 hours 15% of the daunomycin was converted to doxorubicin. The control cultures which lacked the plasmid containing doxA did not convert any of the daunomycin.

Example 14

50 ml cultures of Streptomyces sp. strain C5(pANT195) and Streptomyces sp. strain C5(pANT849) as a control, were grown at 28° C. for 72 hours in NDYE medium as described in Example 1. After 72 hours, 100 mg of unlabelled daunomycin and 5 mCi of $^3$H-daunomycin, having a specific radioactivity of 5.0 Ci/mmol, were added to each culture and they were incubated for another 48 hours. The cultures were extracted as described in Example 1 and analyzed by TLC and autoradiography.

The cultures of containing plasmid pANT195 converted approximately 5% of the radiolabelled daunomycin to doxorubicin. No other products other than the substrate daunomycin and doxorubicin were observed in these cultures. The control cultures converted approximately 90% of the radiolabelled daunomycin to baumycin A1 and baumycin A2.

Example 15

50 ml cultures of Streptomyces sp. strain C5, which does not appear to synthesize doxorubicin, and the following mutants of Streptomyces sp. strain C5: SC5-dauA74, SC5-dauCE147, SC5-dauE24, and SC5-dauH54, were grown for 48 hours in NDYE medium. These mutants do not synthesize daunomycin. At 48 hours, 100 mg of daunomycin was added for a final concentration of 2 mg/ml, and the cultures were incubated for 36 hours. The products were extracted as in Example 1 and subjected to HPLC analysis.

All Streptomyces sp. strain C5 cultures, each of which lacked a plasmid containing doxA, converted about 10% of the daunomycin to doxorubicin. Baumycins A1 and A2 were also detected.

Example 16

The procedure of Example 4 was repeated except that the cultures were then incubated for 48 hours with 100 mg, for a final concentration of 2ug/ml of one of the following: carminomycin, idarubicin, daunomycinone, or carminomycinone.

Incubation of *S. lividans* TK24(pANT195) cultures with carminomycin or idarubicin, resulted in greater than 85% recovery of carminomycin and idarubicin. The cultures which contained plasmid pANT195 converted 100% of the daunomycinone to 13-hydroxydaunomycinone and 100% of the carminomycinone to 13-hydroxycarminomycinone. The control cultures, which lack the doxA gene, converted 100% of the carminomycin, idarubicin, daunomycinone, and carminomycinone to their 13-dihydro derivatives.

Example 17

The procedure of Example 4 was repeated except that the cultures received 100 mg of 13-dihydrocarminomycin rather than daunomycin. The cultures were then incubated for 36 hours and analyzed by TLC and HPLC.

The cultures containing plasmid pANT195 converted 100% of the 13-dihydrocarminomycin to carminomycin. No other products were observed. In the control culture, none of the 13-dihydrocarminomycin was converted. The doxA gene confers the ability to oxidize the C-13 hydroxyl function of the 13-dihydro-carminomycin to a keto function.

Novel Synthesis of 13-deoxycarminomycin and 13-deoxydaunomycin

Example 18 e-Rhodomycin D compound was converted to both 13-deoxycarminomycin and 13-deoxydaunomycin, by host microorganisms containing plasmid which contains the Streptomyces sp. strain C5 dauP gene which encodes e-rhodomycin D esterase and the Streptomyces sp. strain C5 dauK gene which encodes carminomycin 4-O-methyltransferase.

Figure 12:
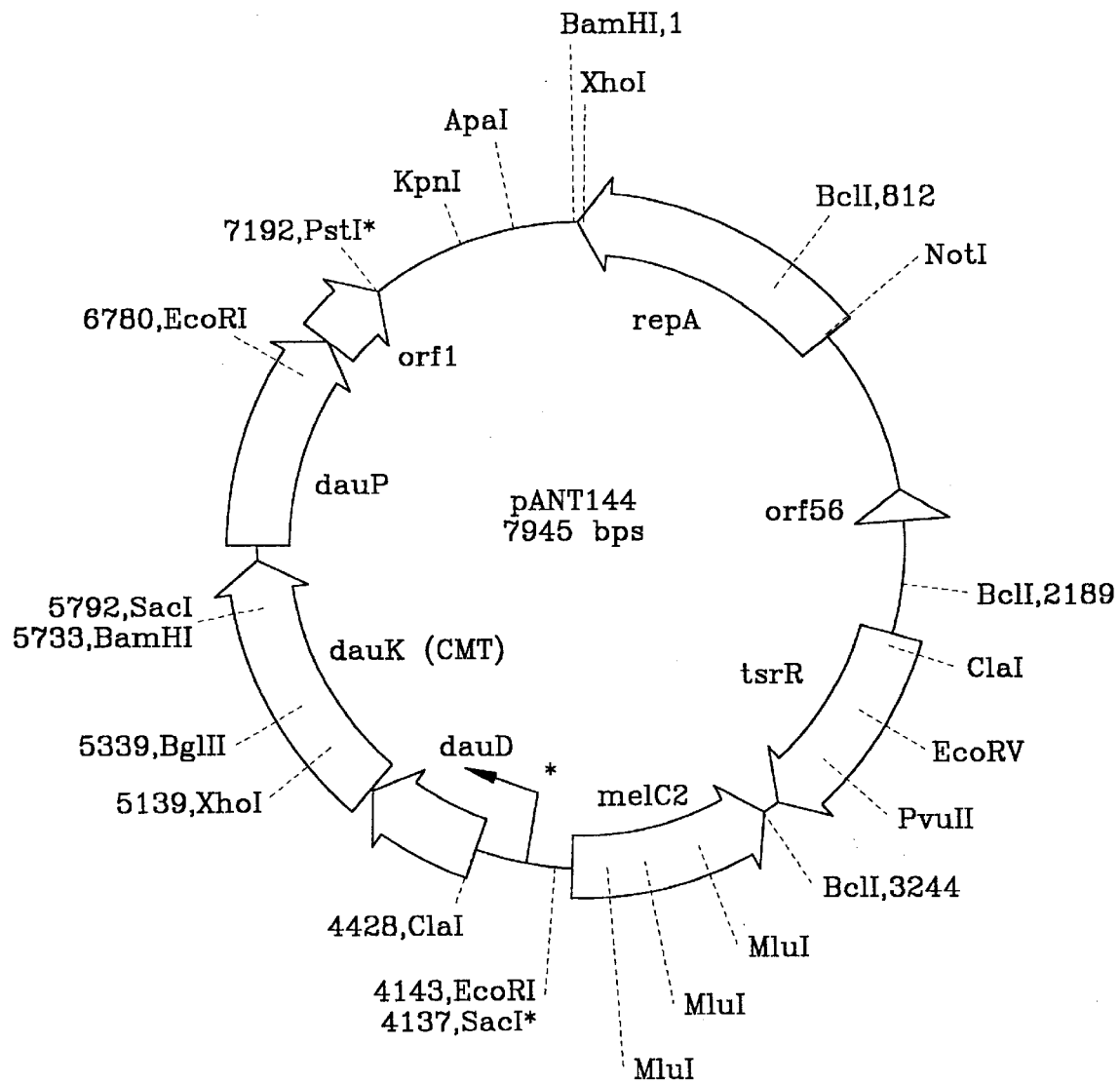
FIG. 12 shows a plasmid map of pANT144.

Plasmid pANT144 as shown in FIG. 12, and described in Dickens, M. L., et. al., (1995) "Analysis of Clustered Genes Encoding both Early and Late Steps in Daunomycin Biosynthesis by Streptomyces sp. strain C5 " *J. Bacteriol.* . volume 177, pages 536–543, was introduced into *S. lividans* TK24 by protoplast transformation. *S. lividans* TK24 (pANT144) was grown for 48 hours in 50 ml of YEME medium containing 10 mg/ml of thiostrepton and then used to inoculate 450 ml of the YEME medium which contained 10 mg/ml of thiostrepton for a total culture volume of 500 ml, in a two liter flask. The resultant 500 ml culture was incubated for 48 hours at 28° C. as in Example 1. Next, 5.0 mg of e-rhodomycin D, the glycone of e-rhodomycinone, from the National Cancer Institute, Drug Synthesis and Chemistry Branch, Bethesda, Md. designated compound #263854-H, were added to the culture for a final concentration of 10 mg/ml and the cultures were incubated for an additional 48 hours. The culture then was adjusted to pH 8.5, and then extracted twice, each with 1 volume of chloroform:methanol (9:1) as in Example 3. The organic extract was reduced to dryness, reconstituted in 500 mL of chloroform:methanol (9:1), filtered, back extracted, dried, and reconstituted in 2.0 ml of methanol. The extract was separated and extracted as in Example 2. $R_f$ values for 13-deoxycarminomycin and 13-deoxydaunomycin were approximately 0.60 and 0.64, respectively. The 13-deoxycarminomycin and 13-deoxydaunomycin were reduced to dryness and each was brought up again in 50 ml of methanol.

Methods of Producing Anthracyclines Employing Daunomycin C-14 Hydroxylase

Example 19

904 ml of the daunomycin C-14 hydroxylase produced according to the method of Example B, containing approximately 1 mg of total protein, was incubated in a 16 mm well of a 24 well culture plate at 30° C. with shaking for 2 hours with 25 mg in 5 ml of either daunomycin, 13-dihydrodaunomycin, or 13-dihydrocarminomycin. The final volume of each well was 1.0 ml; 0.1M sodium phosphate buffer at pH 7.5, was added to bring the total volume to 1 ml, as needed. After 2 hours of incubation, the pH of each reaction mixture was increased to pH 8.5 using 1 M NaOH and each was extracted twice each with 500 ml of chloroform: methanol (9:1). The organic layers were combined, reduced to dryness, reconstituted in 10 ml of methanol, separated and analyzed by TLC as in Example 1.

The daunomycin C-14 hydroxylase converted 50% of the 13-dihydrocarminomycin to carminomycin and 50% of the 13-dihydrodaunomycin to daunomycin.

Example 20

The procedure of example 19 was repeated except that 10 ml of NADH, 1 mM final concentration; 10 ml of NADPH, 1 mM final concentration, were added.

The daunomycin C-14 hydroxylase converted 100% of the 13-dihydrocarminomycin to carminomycin and 100% of the 13-dihydrodaunomycin to daunomycin.

Example 21

The procedure of Example 20 was repeated except that the following reagents, available from Sigma Chemical Co., were added: 20 ml of glucose-6-phosphate; 10 mM final concentration; 10 ml of NADP$^+$, 1 mM final concentration; 1.0 ml of glucose-6-phosphate dehydrogenase; 0.84 units, final activity; 20 ml of spinach ferredoxin, 44 mg final concentration; and 10 ml of spinach ferredoxin-NADP$^+$ reductase, 0.05 units final activity. The glucose-6-phosphate, glucose-6-phosphate dehydrogenase and NADP$^+$ constitute a "NADPH-regenerating system". After 2 hours of incubation, the extracts were extracted and analyzed by TLC and HPLC.

The daunomycin C-14 hydroxylase converted 100% of the 13-dihydrocarminomycin to carminomycin and 100% of the 13-dihydrodaunomycin to daunomycin, as shown by TLC. HPLC revealed the conversion of about 5% of the daunomycin to doxorubicin.

Example 22

The procedure of Example 21 was repeated, except 10 ml of flavin adenine mononucleotide from Sigma, 10 mg final concentration; and 10 mg in 10 ml, flavin adenine dinucleotide, were also added.

100% of the 13-dihydrocarminomycin was converted to carminomycin and 100% of the 13-dihydrodaunomycin was converted to daunomycin by the daunomycin C-14 hydroxylase. Doxorubicin was not detected using TLC.

Example 23

The procedure of Example 20 was repeated except that different anthracyclines were used, incubation was for 1 hour and 10 ml of NADP$^+$, 1 mM final concentration was added. 25 mg in 5 ml the following anthracyclines were used: either e-rhodomycin D, 13-deoxydaunomycin from example 18, or 13-deoxycarminomycin, from example 18.

About 20% of the 13-deoxycarminomycin was converted to 13-dihydrocarminomycin and about 80% was converted to carminomycin; and 13-deoxydaunomycin was converted to about 20% 13-dihydrodaunomycin and about 80% daunomycin. The e-rhodomycin D did not appear to be converted.

Thus, the daunomycin C-14 hydroxylase converted 13-deoxycarminomycin to 13-dihydrocarminomycin and carmninomycin; 13-dihydrocarminomycin to carminomycin; 13-deoxydaunomycin to 13-dihyrodaunomycin and daunomycin; and 1 3-dihydrodaunomycin to daunomycin. Thus, daunomycin C-14 hydroxylase catalyzes the oxidation of the C-13 methylene to a C-13 hydroxyl function, and catalyzes the oxidation of the C-13 hydroxyl function to C-13 keto function. The daunomycin C-14 hydroxylase is useful for making 13-dihydrocarminomycin, carminomycin, 13-dihydrodaunomycin and daunomycin.

Example 24

The procedure of Example 22 was repeated except that the daunomycin C-14 hydroxylase was incubated with daunomycin for 18 hours rather than 2 hours and in 25 ml erylenmyer flasks shaken at 250 rpm on a rotary shaker.

Doxorubicin was not detected by HPLC or TLC.

Example 25

The procedure of Example 24 was repeated except that the reagent volumes were tripled. The reagent concentrations however were not increased.

Approximately 5% of the daunomycin was converted to doxorubicin as determined by a HPLC.

Example 26

The procedure of Example 24 was repeated except that the reagent volumes were quintupled. The reagent concentrations however, were not increased.

Approximately 20 to 25% of the daunomycin was converted to doxorubicin, as determined by HPLC.

The present invention includes: the DNA sequences encoding a protein daunomycin C-14 hydroxylase, which adds a hydroxyl group to carbon 14 of daunomycin; the messenger RNA transcript of such DNA sequence; and an isolated protein which adds a hydroxyl group to carbon 14 of daunomycin.

For example, the DNA sequences include: DNA molecules which, but for the degeneracy of the genetic code would hybridize to DNA encoding the daunomycin C-14 hydroxylase, thus the degenerate DNA which encodes the daunomycin C-14 hydroxylase protein; DNA strands complementary to: DNA sequences encoding the daunomycin C-14 hydroxylase protein including DNA in FIGS. 3, 6, 9 and 11; heterologous DNA having substantial sequence homology to the DNA encoding the daunomycin C-14 hydroxylase protein, including the DNA sequences in FIGS. 3, 6, 9 and 11 or portions thereof.

The daunomycin C-14 hydroxylase protein includes, for example, the daunomycin C-14 hydroxylase protein of strains other than Streptomyces sp. strain C5; proteins having 75% homology to the proteins in FIGS. 3, 6, 9 and 11, and proteins or portions thereof having substantially the same amino acid sequence as shown in FIGS. 3, 6, 9 and 11.

What is claimed is:

1. An isolated daunomycin C-14 hydroxylase which converts daunomycin to doxorubicin, wherein said daunomycin C-14 hydroxylase is from Streptomyces sp. strain C5.

2. The protein of claim 1 further comprising a leader sequence encoding six histidine residues.

3. The isolated daunomycin C-14 hydroxylase of claim 1, wherein said daunomycin C-hydroxylase has the amino acid sequence set forth in SEQ ID NO:5.

4. The isolated daunomocyin C-14 hydroxylase of claim 3 further comprising a leader sequence encoding six histidine residues.

* * * * *

UNITED STATES PATENT AND TRADEMARK OFFICE
CERTIFICATE OF CORRECTION

PATENT NO. : 5,962,293
APPLICATION NO. : 09/096982
DATED : October 5, 1999
INVENTOR(S) : Strohl et al.

Page 1 of 1

It is certified that error appears in the above-identified patent and that said Letters Patent is hereby corrected as shown below:

In the Specification

Column 1, Line 8 add Government Support Clause:
--This invention was made with government support under grant number 9019585 awarded by the National Science Foundation. The government has certain rights in the invention.--

Signed and Sealed this
Seventeenth Day of November, 2020

Andrei Iancu
*Director of the United States Patent and Trademark Office*

```
                          SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:1:

GACATGCATG CGGAGGGGTG CCTC                                              24

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

GACGCAGCTC CGGAACGGGG                                                   20

(2) INFORMATION FOR SEQ ID NO:3:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

GCATGCGAAT TCAGATCTAG AGCTCAAGCT TTAAACTAGT TAACGCGT                    48

(2) INFORMATION FOR SEQ ID NO:4:
```

(i) SEQUENCE CHARACTERISTICS:
            (A) LENGTH: 3196 base pairs
            (B) TYPE: nucleic acid
            (C) STRANDEDNESS: double
            (D) TOPOLOGY: linear (ii) MOLECULE TYPE: DNA (genomic)

(ix) FEATURE:
            (A) NAME/KEY: mat_peptide
            (B) LOCATION: 1498..2764

(ix) FEATURE:
            (A) NAME/KEY: CDS
            (B) LOCATION: 1498..2764

(xi) SEQUENCE DESCRIPTION: SEQ ID NO:4:

```
GGTACCCGCG CATCGATGTC ATGGCCGGCA ACGCCGGCGG CATGTTCTGG TCGCGCACCA      60

CGACCCAGGA CGGGTTCGAG GCCACCCTCC AGGTCAATCA TCTCGCGGGC TTCCTGCTGG     120

CACGGCTGCT GCGGGAGCGG CTCGCGGGCG GGCGGTTGAT CCTCACCTCG TCCGACGCGT     180

ACACCCAGGG CCGGATCGAC CCGGACGATC TCAACGGCGA CCGTCACCGC TACAGCGCGG     240

GCCAGGCGTA CGGCACGTCC AAACAGGCCA ACATCATGAC CGCCACGGAG GCCGCCCGGC     300

GCTGGCCGGA CGTGCTGACG GTCAGCTACC ACCCCGGCGA GGTCCGCACC CGCATCGGGC     360

GGGGCACAGT CGCCTCGACC TACTTCCGGT TCAACCCCTT CCTGCGGTCC GCGGCCAAGG     420

GCGCCGACAC TCTCGTGTGG CTGGCGGCCG CGCCGGCCGA GGAGTTGACC ACGGGCGGCT     480

ACTACAGCGA CCGGCGGCTG TCCCCGGTGA GCGGCCCGAC CGCCGACGCC GGCCTCGCGG     540

CCAAGCTCTG GGAGGCCAGC GCGGCCGCCG TCGGCCACAC CGCGCGCTGA CCGCGGCGGG     600

CCTCCCCGCC CGCATGCCCG TCTCATCCGC GAGCGCAGAC GCTCGTGTGC CGATCCGTCG     660

AAAGGAACGA TTCGTGACCA GGTTCGCGCC CGGCGCCCCC GCATGGTTCG ACCTCGGGTC     720

GCCCGATGTC GCCGCCTCGG CCGACTTCTA CACCGGCCTC TTCGCGTGGA CCGCGACCGT     780

GGTCAGCGAC CCGGGTGCCG GGGGATACAC TACTTTCAGC TCCGACGGGA AGCCTGTCGC     840

CGCGGTCGCC CGCCATCAGA TCGACACGCC CTACCACCGT CCGTACGGGC CCGGCAAGCA     900

CCAGCACGGC ATGCCGGCCA TCTGGACCGT GTACTTCGCC ACCAACGACG CCGACGCACT     960

GACCAAACGG GTCGAAGCGG CGGGTGGCGA CGTCATCATG CACCCGATGG ACGTCCTCGG    1020

TCTCGGCCGG ATGGCGGTCT TCGCCGACCC ATCGGGGGCC GCGTTCGCGG TGTGGCGCAA    1080

GGGCGTCATG GAGGGCGCGG AGGTGACGGG CGTGCCCGGC TCGGTCGGCT GGGTGGAACT    1140

GGTGACCGAC GACATCGGGA CCGCCCGTGG CTTCTACCGT GCGACCCTCG GCCTGGCTCC    1200

GGCCGACACC GGACGCAAGG GCGTCACCGA CCCGGTTTGG CACATCCATG ACACACCGGT    1260

CGCCGGCACC CGGGAACTGG GCACGACCGG CGCGGTACGG CCCCACTGGG CCGTGCTGTT    1320

CTCCGTGCAC GACTGCGACG CGACGGTCCG GCGGGCCGTC GAACTCGGCG GCTCCGTCGA    1380

GAACGAGCCC GTCGACACCC CCAGGGGGCG GCGGGCGGAC CTGCTCGACC CGCACGGGGC    1440

CGGCTTCTCG GTGGTCGAAC TGCGGGAGGC GTACCCCGCG GCGGCGGACG GTGCCTC       1497

ATG AGC GGC GAG GCG CCG CGG GTG GCC GTC GAC CCG TTC TCG TGT CCC      1545
Met Ser Gly Glu Ala Pro Arg Val Ala Val Asp Pro Phe Ser Cys Pro
 1               5                  10                  15

ATG ATG ACC ATG CAG CGC AAA CCC GAG GTG CAC GAC GCA TTC CGA GAG      1593
Met Met Thr Met Gln Arg Lys Pro Glu Val His Asp Ala Phe Arg Glu
            20                  25                  30

GCG GGC CCC GTC GTC GAG GTG AAC GCC CCC GCG GGC GGA CCC GCC TGG      1641
Ala Gly Pro Val Val Glu Val Asn Ala Pro Ala Gly Gly Pro Ala Trp
        35                  40                  45
```

| | | |
|---|---|---|
| GTC ATC ACC GAT GAC GCC CTC GCC CGC GAG GTG CTG GCC GAT CCC CGG | 1689 | |
| Val Ile Thr Asp Asp Ala Leu Ala Arg Glu Val Leu Ala Asp Pro Arg | | |
| 50 55 60 | | |
| TTC GTG AAG GGA CCC GAT CTC GCG CCC ACC GCC TGG CGG GGG GTG GAC | 1737 | |
| Phe Val Lys Gly Pro Asp Leu Ala Pro Thr Ala Trp Arg Gly Val Asp | | |
| 65 70 75 80 | | |
| GAC GGT CTC GAC ATC CCC GTT CCG GAG CTG CGT CCG TTC ACG CTC ATC | 1785 | |
| Asp Gly Leu Asp Ile Pro Val Pro Glu Leu Arg Pro Phe Thr Leu Ile | | |
| 85 90 95 | | |
| GCC GTG GAC GGT GAG GAC CAC CGG CGT CTG CGC CGC ATC CAC GCA CCG | 1833 | |
| Ala Val Asp Gly Glu Asp His Arg Arg Leu Arg Arg Ile His Ala Pro | | |
| 100 105 110 | | |
| GCG TTC AAC CCG CGC CGG CTG GCC GAG CGG ACG GAT CGC ATC GCC GCC | 1881 | |
| Ala Phe Asn Pro Arg Arg Leu Ala Glu Arg Thr Asp Arg Ile Ala Ala | | |
| 115 120 125 | | |
| ATC GCC GAC CGG CTG CTC ACC GAA CTC GCC GAC TCC TCC GAC CGG TCG | 1929 | |
| Ile Ala Asp Arg Leu Leu Thr Glu Leu Ala Asp Ser Ser Asp Arg Ser | | |
| 130 135 140 | | |
| GGC GAA CCG GCC GAG CTG ATC GGC GGC TTC GCG TAC CAC TTC CCG CTG | 1977 | |
| Gly Glu Pro Ala Glu Leu Ile Gly Gly Phe Ala Tyr His Phe Pro Leu | | |
| 145 150 155 160 | | |
| TTG GTC ATC TGC GAA CTG CTC GGC GTG CCG GTC ACC GAT CCG GCA ATG | 2025 | |
| Leu Val Ile Cys Glu Leu Leu Gly Val Pro Val Thr Asp Pro Ala Met | | |
| 165 170 175 | | |
| GCC CGC GAG GCC GTC GGC GTG CTC AAG GCA CTC GGC CTC GGC GGC CCG | 2073 | |
| Ala Arg Glu Ala Val Gly Val Leu Lys Ala Leu Gly Leu Gly Gly Pro | | |
| 180 185 190 | | |
| CAG AGC GCC GGC GGT GAC GGC ACG GAC CCT GCC GGG GAC GTG CCG GAC | 2121 | |
| Gln Ser Ala Gly Gly Asp Gly Thr Asp Pro Ala Gly Asp Val Pro Asp | | |
| 195 200 205 | | |
| ACG TCG GCG CTG GAG AGC CTT CTC CTC GAA GCC GTG CAC GCG GCC CGG | 2169 | |
| Thr Ser Ala Leu Glu Ser Leu Leu Leu Glu Ala Val His Ala Ala Arg | | |
| 210 215 220 | | |
| CGG AAA GAC ACC CGG ACC ATG ACC CGC GTG CTC TAT GAA CGC GCA CAG | 2217 | |
| Arg Lys Asp Thr Arg Thr Met Thr Arg Val Leu Tyr Glu Arg Ala Gln | | |
| 225 230 235 240 | | |
| GCA GAG TTC GGC TCG GTC TCC GAC GAC CAG CTC GTC TAC ATG ATC ACC | 2265 | |
| Ala Glu Phe Gly Ser Val Ser Asp Asp Gln Leu Val Tyr Met Ile Thr | | |
| 245 250 255 | | |
| GGA CTC ATC TTC GCC GGC CAC GAC ACC ACC GGC TCG TTC CTG GGC TTC | 2313 | |
| Gly Leu Ile Phe Ala Gly His Asp Thr Thr Gly Ser Phe Leu Gly Phe | | |
| 260 265 270 | | |
| CTG CTT GCG GAG GTC CTG GCG GGC CGT CTC GCG GCG GAC GCC GAC GGG | 2361 | |
| Leu Leu Ala Glu Val Leu Ala Gly Arg Leu Ala Ala Asp Ala Asp Gly | | |
| 275 280 285 | | |
| GAC GCC ATC TCC CGG TTC GTG GAG GAG GCG CTG CGC CAC CAC CCG CCG | 2409 | |
| Asp Ala Ile Ser Arg Phe Val Glu Glu Ala Leu Arg His His Pro Pro | | |
| 290 295 300 | | |
| GTG CCC TAC TCG TTG TGG AGG TTC GCT GCC ACG GAG GTG GTC ATC CGC | 2457 | |
| Val Pro Tyr Ser Leu Trp Arg Phe Ala Ala Thr Glu Val Val Ile Arg | | |
| 305 310 315 320 | | |
| GGT GTC CGG CTG CCC CGC GGA GCG CCG GTA CTG GTG GAC ATC GAG GGC | 2505 | |
| Gly Val Arg Leu Pro Arg Gly Ala Pro Val Leu Val Asp Ile Glu Gly | | |
| 325 330 335 | | |
| ACC AAC ACC GAC GGC CGC CAT CAC GAC GCC CCG CAC GCT TTC CAC CCG | 2553 | |
| Thr Asn Thr Asp Gly Arg His His Asp Ala Pro His Ala Phe His Pro | | |
| 340 345 350 | | |
| GAC CGC CCT TCG AGG CGG CGG CTC ACC TTC GGC GAC GGG CCG CAC TAC | 2601 | |
| Asp Arg Pro Ser Arg Arg Arg Leu Thr Phe Gly Asp Gly Pro His Tyr | | |
| 355 360 365 | | |

```
TGC ATC GGG GAG CAG CTC GCC CAG CTG GAA TCG CGC ACG ATG ATC GGC         2649
Cys Ile Gly Glu Gln Leu Ala Gln Leu Glu Ser Arg Thr Met Ile Gly
        370                 375                 380

GTA CTG CGC AGC AGG TTC CCC CAA GCC CGA CTG GCC GTG CCG TAC GAG         2697
Val Leu Arg Ser Arg Phe Pro Gln Ala Arg Leu Ala Val Pro Tyr Glu
385                 390                 395                 400

GAG TTG CGG TGG TGC AGG AAG GGG GCC CAG ACA GCG CGG CTC ACT GAC         2745
Glu Leu Arg Trp Cys Arg Lys Gly Ala Gln Thr Ala Arg Leu Thr Asp
                405                 410                 415

CTG CCC GTC TGG CTG CGT T GATGGGCCGA CCGCGACCCG GCACGGGACC              2794
Leu Pro Val Trp Leu Arg
                420

GCCCACCGCC CATCGCGCGG TGGGCGGTCC CGTGCCGGTC GCCCGGTGCG GTCCTCTCCC       2854

GACGCTCGCT CCCCCTGTGA CTTTCTCACA TCGAGACGTG ACGAAATAAT CCCAGCAAGT       2914

GCCATGCACA CTTTCATGGC GGACATTCAC TTGCGAGGAT GGAGTGAGCA CACGGGGCCG       2974

CCCGAGACAC CCTACGGCCG CCGGAAGTAT GCCACCTGTT GACGCGAATG GAACGCCACA       3034

GAGGGAGCAC CGGCAATGCA GATCAATATG TTGGGCCCGC TCGTTGCACA TCACAATGGC       3094

ACGTCGGTGA CCCCGATAGC CAGAAAACCC CGGCAGGTAT TCTCACTGCT CGCTCTTCAG       3154

GCAGGAACCG TCGTTCCGGT CCCCGCGCTG ATGGAGGAGC TC                         3196

(2) INFORMATION FOR SEQ ID NO:5:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:5:

Met Ser Gly Glu Ala Pro Arg Val Ala Val Asp Pro Phe Ser Cys Pro
1               5                   10                  15

Met Met Thr Met Gln Arg Lys Pro Glu Val His Asp Ala Phe Arg Glu
            20                  25                  30

Ala Gly Pro Val Val Glu Val Asn Ala Pro Ala Gly Gly Pro Ala Trp
        35                  40                  45

Val Ile Thr Asp Asp Ala Leu Ala Arg Glu Val Leu Ala Asp Pro Arg
    50                  55                  60

Phe Val Lys Gly Pro Asp Leu Ala Pro Thr Ala Trp Arg Gly Val Asp
65                  70                  75                  80

Asp Gly Leu Asp Ile Pro Val Pro Glu Leu Arg Pro Phe Thr Leu Ile
                85                  90                  95

Ala Val Asp Gly Glu Asp His Arg Leu Arg Arg Ile His Ala Pro
            100                 105                 110

Ala Phe Asn Pro Arg Arg Leu Ala Glu Arg Thr Asp Arg Ile Ala Ala
        115                 120                 125

Ile Ala Asp Arg Leu Leu Thr Glu Leu Ala Asp Ser Ser Asp Arg Ser
    130                 135                 140

Gly Glu Pro Ala Glu Leu Ile Gly Gly Phe Ala Tyr His Phe Pro Leu
145                 150                 155                 160

Leu Val Ile Cys Glu Leu Leu Gly Val Pro Val Thr Asp Pro Ala Met
                165                 170                 175

Ala Arg Glu Ala Val Gly Val Leu Lys Ala Leu Gly Leu Gly Gly Pro
            180                 185                 190

Gln Ser Ala Gly Gly Asp Gly Thr Asp Pro Ala Gly Asp Val Pro Asp
        195                 200                 205
```

```
Thr Ser Ala Leu Glu Ser Leu Leu Glu Ala Val His Ala Ala Arg
    210             215             220

Arg Lys Asp Thr Arg Thr Met Thr Arg Val Leu Tyr Glu Arg Ala Gln
225             230             235             240

Ala Glu Phe Gly Ser Val Ser Asp Asp Gln Leu Val Tyr Met Ile Thr
                245             250             255

Gly Leu Ile Phe Ala Gly His Asp Thr Thr Gly Ser Phe Leu Gly Phe
            260             265             270

Leu Leu Ala Glu Val Leu Ala Gly Arg Leu Ala Ala Asp Ala Asp Gly
        275             280             285

Asp Ala Ile Ser Arg Phe Val Glu Glu Ala Leu Arg His His Pro Pro
    290             295             300

Val Pro Tyr Ser Leu Trp Arg Phe Ala Ala Thr Glu Val Val Ile Arg
305             310             315             320

Gly Val Arg Leu Pro Arg Gly Ala Pro Val Leu Val Asp Ile Glu Gly
                325             330             335

Thr Asn Thr Asp Gly Arg His His Asp Ala Pro His Ala Phe His Pro
            340             345             350

Asp Arg Pro Ser Arg Arg Arg Leu Thr Phe Gly Asp Gly Pro His Tyr
        355             360             365

Cys Ile Gly Glu Gln Leu Ala Gln Leu Glu Ser Arg Thr Met Ile Gly
    370             375             380

Val Leu Arg Ser Arg Phe Pro Gln Ala Arg Leu Ala Val Pro Tyr Glu
385             390             395             400

Glu Leu Arg Trp Cys Arg Lys Gly Ala Gln Thr Ala Arg Leu Thr Asp
                405             410             415

Leu Pro Val Trp Leu Arg
            420

(2) INFORMATION FOR SEQ ID NO:6:

(i) SEQUENCE CHARACTERISTICS:
        (A) LENGTH: 3013 base pairs
        (B) TYPE: nucleic acid
        (C) STRANDEDNESS: double
        (D) TOPOLOGY: linear (ii) MOLECULE TYPE: other nucleic acid (xi) SEQUENCE DESCRIPTION: SEQ ID NO:6:

GCAGGCGGTA CCGCCGACCC GCTGCATCCC CCGCACCGCC GTCCCCCCCC AGGGCATCTC      60

CCGTCGGGTT ACGGGAAGGG GGCCGGGGTA CCCGGTCGTC ACGGGAGGGC TGGGACGAGT     120

GCCCCCGACC CACTGCGTTC CAGCCACTCC CGGTACGCCG GGGCCTGCCG GGCGACCTCC     180

CCGTAGGCCT CCGCGAGGTC GGGGTAGACG CCCTCCAGTT CCGTGTCCGT GCGGGCCGCC     240

AGCAGCAGCC GTACGCCGAG CGGGTCGCCG TGCAGCCGGC GGACGGCCGT CTCGGCGCGG     300

GAGGGCGAGG TCGGCTGGAC CACGGTGACG ACCTCGCCGG TGGCGACCAG GTACGCGGCG     360

GAGTGGTAGT CCCCGTGCAG GATGCGCGAG TCGAGTCCCT CGGCGCGCAG GACCCGGCGC     420

ACCGCGTTCC ACTCGCCGTC GACGGTGGGG TCGATCATCC AGCGGGTCGT GGGCCAGGTC     480

GGCGAGGCGT ACGACGTGGC TTCGGCGGCC GGGTGGTCGG CCGGCAGGCA GACGAACTGC     540

GGTTCCCGCT GGACCAGTAC GCGGACCCGG AGCCCTTCGG GGACGCGCAG GCTGCCCTCG     600

ACCTCGTGCA CGAAGGCGAC GTCGAGGTGG CCGTCGGCCA CCATGCGCAG CAGGGCGTTG     660

GCGGAGACGT CCATGTGCAG GGTGGGTTCC TGCCAGTGCC GGAGCCGGCG CAGCCAGCCC     720
```

```
GCCAGGGCCC GGCTGGCCGT GGAGCCGACG CGCAGGCTGG CGTCCGCGAC GGCGGCGGCG       780

CGGGCCTCGC TGACGAGGGA GCACAATTCG GCCACCAGGG GGCGGGCACG ACTGAGAACC       840

AGCCGGCCCA GCGGTGTGGG GCGGCAGCCG GTGCGGGCCC GGACGAACAG GGCACGGCCC       900

AGCTCGTGTT GGATGCGCCG CAGCTGCGTG CTCAACGAGG GCTGTGTCAC TCCCAGTTGG       960

CGTGCCGCGC GGTGCAGGCT GCCGGTGTCG GCGATGGCGC ACAGCGCCCT GAGGTGCCTG      1020

ACCTCAAGCT CCATGTCCTG GGAGGGTAAG GCGGAAGTTC AGCTTTCACC AGACATACAA      1080

AATGGCGACC GATCAGGACC ATCGGGCCTT CACGGCGCGA GGCGTCGGCC CGGATCGGCA      1140

GGGGCCCCGG CCGGGGCCGC CGGGCAGGGC GGCGCAGGTG GGGACGGAGG GGGATAGGGC      1200

GGCCCTATCG GCGGTTGCCA TCATCACAAC GGCCGTACGG GCACGGACAC TCACGATGTC      1260

TGACTCATCC CCCCACCTCG AGGAGTCATC GATGCGCATG CGGAGGGGTG CCTCATCAGC      1320

GGCCCTATCG GCGGTTGCCA TCATCACAAC GGCCGTACGG GCACGGACAC TCACGATGTC      1380

TGACTCATCC CCCCACCTCG AGGAGTCATC GATGCGCATG CGGAGGGGTG CCTCATGAGC      1440

GCGGGCGGAC CCGCCTGGGT CATCACCGAT GACGCCCTCG CCCGCGAGGT GCTGGCCGAT      1500

CCCCGGTTCG TGAAGGACCC CGATCTCGCG CCCACCGCCT GGCGGGGGT GGACGACGGT      1560

CTCGACATCC CCGTTCCGGA GCTGCGTCCG TTCACGCTCA TCGCCGTGGA CGGTGAGGAC      1620

CACCGCCGTC TGCGCCGCAT CCACGCACCG GCGTTCAACC CGCGCCGGCT GGCCGAGCGG      1680

ACGGATCGCA TCGCCGCCAT CGCCGACCGG CTGCTCACCG AACTCGCCGA CTCCTCCGAC      1740

CGGTCGGGCG AACCGGCCGA GCTGATCGGC GGCTTCGCGT ACCACTTCCC GCTGTTGGTC      1800

ATCTGCGAAC TGCTCGGCGT GCCGGTCACC GATCCGGCAA TGGCCCGCGA GGCCGTCGGC      1860

GTGCTCAAGG CACTCGGCCT CGGCGGCCCG CAGAGCGCCG GCGGTGACGG CACGGACCCT      1920

GCCGGGGACG TGCCGGACAC GTCGGCGCTG GAGAGCCTTC TCCTCGAAGC CGTGCACGCG      1980

GCCCGGCGGA AAGACACCCG GACCATGACC CGCGTGCTCT ATGAACGCGC ACAGGCAGAG      2040

TTCGGCTCGG TCTCCGACGA CCAGCTCGTC TACATGATCA CCGGACTCAT CTTCGCCGGC      2100

CACGACACCA CCGGCTCGTT CCTGGGCTTC CTGCTTGCGG AGGTCCTGGC GGGCCGTCTC      2160

GCGGCGGACG CCGACGGGGA CGCCATCTCC CGGTTCGTGG AGGAGGCGCT GCGCCACCAC      2220

CCGCCGGTGC CCTACACGTT GTGGAGGTTC GCTGCCACGG AGGTGGTCAT CCGCGGTGTC      2280

CGGCTGCCCC GCGGAGCGCC GGTACTGGTG GACATCGAGG GCACCAACAC CGACGGCCGC      2340

CATCACGACG CCCCGCACGC TTTCCACCCG GACCGCCCTT CGAGGCGGCG GCTCACCTTC      2400

GGCGACGGGC CGCACTACTG CATCGGGGAG CAGCTCGCCC AGCTGGAATC GCGCACGATG      2460

ATCGGCGTAC TGCGCAGCAG GTTCCCCCAA GCCCGACTGG CCGTGCCGTA CGAGGAGTTG      2520

CGGTGGTGCA GGAAGGGGGC CCAGACAGCG CGGCTCACTG ACCTGCCCGT CTGGCTGCGT      2580

TGATGGGCCG ACCGCGACCC GGCACGGGAC CGCCCACCGC CCATCGCGCG GTGGGCGGTC      2640

CCGTGCCGGT CGCCCGGTGC GGTCCTCTCC CGACGCTCGC TCCCCCTGTG ACTTTCTCAC      2700

ATCGAGACGT GACGAAATAA TCCCAGCAAG TGCCATGCAC ACTTTCATGG CGGACATTCA      2760

CTTGCGAGGA TGGAGTGAGC ACACGGGGCC GCCCGAGACA CCCTACGGCC GCCGGAAGTA      2820

TGCCACCTGT TGACGCGAAT GGAACGCCAC AGAGGGAGCA CCGCCAATGC AGATCAATAT      2880

GTTGGGCCCG CTCGTTGCAC ATCACAATGG CACGTCGGTG ACCCCGATAG CCAGAAAACC      2940

CCGGCAGGTA TTCTCACTGC TCGCTCTTCA GGCAGGAACC GTCGTTCCGG TCCCCGCGCT      3000

GATGGAGGAG CTC                                                        3013
```

(2) INFORMATION FOR SEQ ID NO:7:

(i) SEQUENCE CHARACTERISTICS:
  (A) LENGTH: 2081 base pairs
  (B) TYPE: nucleic acid
  (C) STRANDEDNESS: double
  (D) TOPOLOGY: linear (ii) MOLECULE TYPE: DNA (genomic)

(ix) FEATURE:
  (A) NAME/KEY: CDS
  (B) LOCATION: 227..1649

(xi) SEQUENCE DESCRIPTION: SEQ ID NO:7:

```
TGTTGACAAT TAATCATCCG GCTCGTATAA TGTGTGGAAT TGTGAGCGGA TAACAATTTC    60

ACACAGGAAA CAGCGCCGCT GAGAAAAAGC GAAGCGGCAC TGCTCTTTAA CAATTTATCA   120

GACAATCTGT GTGGGCACTC GACCGGAATT GGGCATCGAT TAACTTTATT ATTAAAAATT   180

AAAGAGGTAT ATATTAATGT ATCGATTAAA TAAGGAGGAA TAAACC ATG GGG GGT      235
                                                 Met Gly Gly
                                                  1

TCT CAT CAT CAT CAT CAT CAT GGT ATG GCT AGC ATG ACT GGT GGA CAG    283
Ser His His His His His His Gly Met Ala Ser Met Thr Gly Gly Gln
    5               10                  15

CAA ATG GGT CGG GAT CTG TAC GAC GAT GAT AAG GAT CGA TGG ATC        331
Gln Met Gly Arg Asp Leu Tyr Asp Asp Asp Lys Asp Arg Trp Ile
 20              25                  30                  35

CGA CCT CGA GAT CTG CAG ATG GTA CCA TAT GGG AAT TCG GAG GGG TGC    379
Arg Pro Arg Asp Leu Gln Met Val Pro Tyr Gly Asn Ser Glu Gly Cys
             40                  45                  50

CTC ATG AGC GGC GAG GCG CCG CGG GTG GCC GTC GAC CCG TTC TCG TGT    427
Leu Met Ser Gly Glu Ala Pro Arg Val Ala Val Asp Pro Phe Ser Cys
         55                  60                  65

CCC ATG ATG ACC ATG CAG CGC AAA CCC GAG GTG CAC GAC GCA TTC CGA    475
Pro Met Met Thr Met Gln Arg Lys Pro Glu Val His Asp Ala Phe Arg
     70                  75                  80

GAG GCG GGC CCC GTC GTC GAG GTG AAC GCC CCC GCG GGC GGA CCC GCC    523
Glu Ala Gly Pro Val Val Glu Val Asn Ala Pro Ala Gly Gly Pro Ala
 85                  90                  95

TGG GTC ATC ACC GAT GAC GCC CTC GCC CGC GAG GTG CTG GCC GAT CCC    571
Trp Val Ile Thr Asp Asp Ala Leu Ala Arg Glu Val Leu Ala Asp Pro
100                 105                 110                 115

CGG TTC GTG AAG GGA CCC GAT CTC GCG CCC ACC GCC TGG CGG GGG GTG    619
Arg Phe Val Lys Gly Pro Asp Leu Ala Pro Thr Ala Trp Arg Gly Val
             120                 125                 130

GAC GAC GGT CTC GAC ATC CCC GTT CCG GAG CTG CGT CCG TTC ACG CTC    667
Asp Asp Gly Leu Asp Ile Pro Val Pro Glu Leu Arg Pro Phe Thr Leu
         135                 140                 145

ATC GCC GTG GAC GGT GAG GAC CAC CGG CGT CTG CGC CGC ATC CAC GCA    715
Ile Ala Val Asp Gly Glu Asp His Arg Arg Leu Arg Arg Ile His Ala
     150                 155                 160

CCG GCG TTC AAC CCG CGC CGG CTG GCC GAG CGG ACG GAT CGC ATC GCC    763
Pro Ala Phe Asn Pro Arg Arg Leu Ala Glu Arg Thr Asp Arg Ile Ala
165                 170                 175

GCC ATC GCC GAC CGG CTG CTC ACC GAA CTC GCC GAC TCC TCC GAC CGG    811
Ala Ile Ala Asp Arg Leu Leu Thr Glu Leu Ala Asp Ser Ser Asp Arg
180                 185                 190                 195

TCG GGC GAA CCG GCC GAG CTG ATC GGC GGC TTC GCG TAC CAC TTC CCG    859
Ser Gly Glu Pro Ala Glu Leu Ile Gly Gly Phe Ala Tyr His Phe Pro
             200                 205                 210

CTG TTG GTC ATC TGC GAA CTG CTC GGC GTG CCG GTC ACC GAT CCG GCA    907
Leu Leu Val Ile Cys Glu Leu Leu Gly Val Pro Val Thr Asp Pro Ala
         215                 220                 225
```

```
ATG GCC CGC GAG GCC GTC GGC GTG CTC AAG GCA CTC GGC CTC GGC GGC       955
Met Ala Arg Glu Ala Val Gly Val Leu Lys Ala Leu Gly Leu Gly Gly
        230                 235                 240

CCG CAG AGC GCC GGC GGT GAC GGC ACG GAC CCT GCC GGG GAC GTG CCG      1003
Pro Gln Ser Ala Gly Gly Asp Gly Thr Asp Pro Ala Gly Asp Val Pro
245                 250                 255

GAC ACG TCG GCG CTG GAG AGC CTT CTC CTC GAA GCC GTG CAC GCG GCC      1051
Asp Thr Ser Ala Leu Glu Ser Leu Leu Leu Glu Ala Val His Ala Ala
260                 265                 270                 275

CGG CGG AAA GAC ACC CGG ACC ATG ACC CGC GTG CTC TAT GAA CGC GCA      1099
Arg Arg Lys Asp Thr Arg Thr Met Thr Arg Val Leu Tyr Glu Arg Ala
            280                 285                 290

CAG GCA GAG TTC GGC TCG GTC TCC GAC GAC CAG CTC GTC TAC ATG ATC      1147
Gln Ala Glu Phe Gly Ser Val Ser Asp Asp Gln Leu Val Tyr Met Ile
                295                 300                 305

ACC GGA CTC ATC TTC GCC GGC CAC GAC ACC ACC GGC TCG TTC CTG GGC      1195
Thr Gly Leu Ile Phe Ala Gly His Asp Thr Thr Gly Ser Phe Leu Gly
                    310                 315                 320

TTC CTG CTT GCG GAG GTC CTG GCG GGC CGT CTC GCG GCG GAC GCC GAC      1243
Phe Leu Leu Ala Glu Val Leu Ala Gly Arg Leu Ala Ala Asp Ala Asp
    325                 330                 335

GGG GAC GCC ATC TCC CGG TTC GTG GAG GAG GCG CTG CGC CAC CAC CCG      1291
Gly Asp Ala Ile Ser Arg Phe Val Glu Glu Ala Leu Arg His His Pro
340                 345                 350                 355

CCG GTG CCC TAC TCG TTG TGG AGG TTC GCT GCC ACG GAG GTG GTC ATC      1339
Pro Val Pro Tyr Ser Leu Trp Arg Phe Ala Ala Thr Glu Val Val Ile
                360                 365                 370

CGC GGT GTC CGG CTG CCC CGC GGA GCG CCG GTA CTG GTG GAC ATC GAG      1387
Arg Gly Val Arg Leu Pro Arg Gly Ala Pro Val Leu Val Asp Ile Glu
            375                 380                 385

GGC ACC AAC ACC GAC GGC CGC CAT CAC GAC GCC CCG CAC GCT TTC CAC      1435
Gly Thr Asn Thr Asp Gly Arg His His Asp Ala Pro His Ala Phe His
        390                 395                 400

CCG GAC CGC CCT TCG AGG CGG CGG CTC ACC TTC GGC GAC GGG CCG CAC      1483
Pro Asp Arg Pro Ser Arg Arg Arg Leu Thr Phe Gly Asp Gly Pro His
405                 410                 415

TAC TGC ATC GGG GAG CAG CTC GCC CAG CTG GAA TCG CGC ACG ATG ATC      1531
Tyr Cys Ile Gly Glu Gln Leu Ala Gln Leu Glu Ser Arg Thr Met Ile
420                 425                 430                 435

GGC GTA CTG CGC AGC AGG TTC CCC CAA GCC CGA CTG GCC GTG CCG TAC      1579
Gly Val Leu Arg Ser Arg Phe Pro Gln Ala Arg Leu Ala Val Pro Tyr
                440                 445                 450

GAG GAG TTG CGG TGG TGC AGG AAG GGG GCC CAG ACA GCG CGG CTC ACT      1627
Glu Glu Leu Arg Trp Cys Arg Lys Gly Ala Gln Thr Ala Arg Leu Thr
            455                 460                 465

GAC CTG CCC GTC TGG CTG CGT T GATGGGCCGA CCGCGACCCG GCACGGGACC       1679
Asp Leu Pro Val Trp Leu Arg
        470

GCCCACCGCC CATCGCGCGG TGGGCGGTCC CGTGCCGGTC GCCCGGTGCG GTCCTCTCCC    1739

GACGCTCGCT CCCCCTGTGA CTTTCTCACA TCGAGACGTG ACGAAATAAT CCCAGCAAGT    1799

GCCATGCACA CTTTCATGGC GGACATTCAC TTGCGAGGAT GGAGTGAGCA CACGGGGCCG    1859

CCCGAGACAC CCTACGGCCG CCGGAAGTAT GCCACCTGTT GACGCGAATG GAACGCCACA    1919

GAGGGAGCAC CGGCAATGCA GATCAATATG TTGGGCCCGC TCGTTGCACA TCACAATGGC    1979

ACGTCGGTGA CCCCGATAGC CAGAAAACCC CGGCAGGTAT TCTCACTGCT CGCTCTTCAG    2039

GCAGGAACCG TCGTTCCGGT CCCCGCGCTG ATGGAGGAGC TC                       2081
```

-continued (2) INFORMATION FOR SEQ ID NO:8:

(i) SEQUENCE CHARACTERISTICS:
        (A) LENGTH: 474 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Arg Trp Ile Arg Pro Arg Asp Leu Gln Met Val Pro Tyr Gly Asn Ser
            35                  40                  45

Glu Gly Cys Leu Met Ser Gly Glu Ala Pro Arg Val Ala Val Asp Pro
    50                  55                      60

Phe Ser Cys Pro Met Met Thr Met Gln Arg Lys Pro Glu Val His Asp
65                  70                  75                  80

Ala Phe Arg Glu Ala Gly Pro Val Val Glu Val Asn Ala Pro Ala Gly
                85                  90                  95

Gly Pro Ala Trp Val Ile Thr Asp Asp Ala Leu Ala Arg Glu Val Leu
                100                 105                 110

Ala Asp Pro Arg Phe Val Lys Gly Pro Asp Leu Ala Pro Thr Ala Trp
            115                 120                 125

Arg Gly Val Asp Asp Gly Leu Asp Ile Pro Val Pro Glu Leu Arg Pro
            130                 135                 140

Phe Thr Leu Ile Ala Val Asp Gly Glu Asp His Arg Arg Leu Arg Arg
145                 150                 155                 160

Ile His Ala Pro Ala Phe Asn Pro Arg Leu Ala Glu Arg Thr Asp
                165                 170                 175

Arg Ile Ala Ala Ile Ala Asp Arg Leu Leu Thr Glu Leu Ala Asp Ser
            180                 185                 190

Ser Asp Arg Ser Gly Glu Pro Ala Glu Leu Ile Gly Gly Phe Ala Tyr
            195                 200                 205

His Phe Pro Leu Leu Val Ile Cys Glu Leu Leu Gly Val Pro Val Thr
    210                 215                 220

Asp Pro Ala Met Ala Arg Glu Ala Val Gly Val Leu Lys Ala Leu Gly
225                 230                 235                 240

Leu Gly Gly Pro Gln Ser Ala Gly Gly Asp Gly Thr Asp Pro Ala Gly
                245                 250                 255

Asp Val Pro Asp Thr Ser Ala Leu Glu Ser Leu Leu Glu Ala Val
            260                 265                 270

His Ala Ala Arg Arg Lys Asp Thr Arg Thr Met Thr Arg Val Leu Tyr
            275                 280                 285

Glu Arg Ala Gln Ala Glu Phe Gly Ser Val Ser Asp Asp Gln Leu Val
    290                 295                 300

Tyr Met Ile Thr Gly Leu Ile Phe Ala Gly His Asp Thr Thr Gly Ser
305                 310                 315                 320

Phe Leu Gly Phe Leu Leu Ala Glu Val Leu Ala Gly Arg Leu Ala Ala
                325                 330                 335

Asp Ala Asp Gly Asp Ala Ile Ser Arg Phe Val Glu Glu Ala Leu Arg
            340                 345                 350

His His Pro Pro Val Pro Tyr Ser Leu Trp Arg Phe Ala Ala Thr Glu
            355                 360                 365
```

-continued

```
Val Val Ile Arg Gly Val Arg Leu Pro Arg Gly Ala Pro Val Leu Val
    370                 375                 380

Asp Ile Glu Gly Thr Asn Thr Asp Gly Arg His His Asp Ala Pro His
385                 390                 395                 400

Ala Phe His Pro Asp Arg Pro Ser Arg Arg Leu Thr Phe Gly Asp
                405                 410                 415

Gly Pro His Tyr Cys Ile Gly Glu Gln Leu Ala Gln Leu Glu Ser Arg
            420                 425                 430

Thr Met Ile Gly Val Leu Arg Ser Arg Phe Pro Gln Ala Arg Leu Ala
                435                 440                 445

Val Pro Tyr Glu Glu Leu Arg Trp Cys Arg Lys Gly Ala Gln Thr Ala
    450                 455                 460

Arg Leu Thr Asp Leu Pro Val Trp Leu Arg
465                 470
```

(2) INFORMATION FOR SEQ ID NO:9:

(i) SEQUENCE CHARACTERISTICS:
        (A) LENGTH: 443 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Asp Arg Trp Ile Arg Pro Arg Asp Leu Gln Met Val Pro Tyr Gly Asn
1               5                   10                  15

Ser Glu Gly Cys Leu Met Ser Gly Glu Ala Pro Arg Val Ala Val Asp
                20                  25                  30

Pro Phe Ser Cys Pro Met Met Thr Met Gln Arg Lys Pro Glu Val His
            35                  40                  45

Asp Ala Phe Arg Glu Ala Gly Pro Val Val Glu Val Asn Ala Pro Ala
    50                  55                  60

Gly Gly Pro Ala Trp Val Ile Thr Asp Asp Ala Leu Ala Arg Glu Val
65                  70                  75                  80

Leu Ala Asp Pro Arg Phe Val Lys Asp Pro Asp Leu Ala Pro Thr Ala
                85                  90                  95

Trp Arg Gly Val Asp Asp Gly Leu Asp Ile Pro Val Pro Glu Leu Arg
            100                 105                 110

Pro Phe Thr Leu Ile Ala Val Asp Gly Glu Asp His Arg Arg Leu Arg
        115                 120                 125

Arg Ile His Ala Pro Ala Phe Asn Pro Arg Arg Leu Ala Glu Arg Thr
    130                 135                 140

Asp Arg Ile Ala Ala Ile Ala Asp Arg Leu Leu Thr Glu Leu Ala Asp
145                 150                 155                 160

Ser Ser Asp Arg Ser Gly Glu Pro Ala Glu Leu Ile Gly Gly Phe Ala
                165                 170                 175

Tyr His Phe Pro Leu Leu Val Ile Cys Glu Leu Leu Gly Val Pro Val
            180                 185                 190

Thr Asp Pro Ala Met Ala Arg Glu Ala Val Gly Val Leu Lys Ala Leu
        195                 200                 205

Gly Leu Gly Gly Pro Gln Ser Ala Gly Gly Asp Gly Thr Asp Pro Ala
    210                 215                 220

Gly Asp Val Pro Asp Thr Ser Ala Leu Glu Ser Leu Leu Glu Ala
225                 230                 235                 240

Val His Ala Ala Arg Arg Lys Asp Thr Arg Thr Met Thr Arg Val Leu
```

```
                    245                 250                 255
Tyr Glu Arg Ala Gln Ala Glu Phe Gly Ser Val Ser Asp Asp Gln Leu
            260                 265                 270

Val Tyr Met Ile Thr Gly Leu Ile Phe Ala Gly His Asp Thr Thr Gly
        275                 280                 285

Ser Phe Leu Gly Phe Leu Leu Ala Glu Val Leu Ala Gly Arg Leu Ala
    290                 295                 300

Ala Asp Ala Asp Gly Asp Ala Ile Ser Arg Phe Val Glu Glu Ala Leu
305                 310                 315                 320

Arg His His Pro Pro Val Pro Tyr Thr Leu Trp Arg Phe Ala Ala Thr
                325                 330                 335

Glu Val Val Ile Arg Gly Val Arg Leu Pro Arg Gly Ala Pro Val Leu
                340                 345                 350

Val Asp Ile Glu Gly Thr Asn Thr Asp Gly Arg His His Asp Ala Pro
            355                 360                 365

His Ala Phe His Pro Asp Arg Pro Ser Arg Arg Leu Thr Phe Gly
        370                 375                 380

Asp Gly Pro His Tyr Cys Ile Gly Glu Gln Leu Ala Gln Leu Glu Ser
385                 390                 395                 400

Arg Thr Met Ile Gly Val Leu Arg Ser Arg Phe Pro Gln Ala Arg Leu
                405                 410                 415

Ala Val Pro Tyr Glu Glu Leu Arg Trp Cys Arg Lys Gly Ala Gln Thr
            420                 425                 430

Ala Arg Leu Thr Asp Leu Pro Val Trp Leu Arg
            435                 440
```